(12) United States Patent
Endell et al.

(10) Patent No.: US 12,358,983 B2
(45) Date of Patent: Jul. 15, 2025

(54) COMBINATION OF ANTI CD19 ANTIBODY WITH A BCL-2 INHIBITOR AND USES THEREOF

(71) Applicant: Incyte Corporation, Wilmington, DE (US)

(72) Inventors: Jan Endell, Munich (DE); Konstantin Petropoulos, Munich (DE); Peter Kelemen, Munich (DE); Rainer Boxhammer, Aying (DE); Markus Rückert, Kottgeisering (DE)

(73) Assignee: Incyte Corporation, Wilmington, DE (US)

( * ) Notice: Subject to any disclaimer, the term of this patent is extended or adjusted under 35 U.S.C. 154(b) by 85 days.

(21) Appl. No.: 16/342,645

(22) PCT Filed: Oct. 27, 2017

(86) PCT No.: PCT/EP2017/077654
§ 371 (c)(1),
(2) Date: Apr. 17, 2019

(87) PCT Pub. No.: WO2018/078123
PCT Pub. Date: May 3, 2018

(65) Prior Publication Data
US 2019/0241656 A1 Aug. 8, 2019

(30) Foreign Application Priority Data

Oct. 28, 2016 (EP) .................................. 16196184

(51) Int. Cl.
| A61K 39/395 | (2006.01) |
| A61K 9/00 | (2006.01) |
| A61K 31/496 | (2006.01) |
| A61P 35/02 | (2006.01) |
| C07K 16/28 | (2006.01) |

(52) U.S. Cl.
CPC ........ *C07K 16/2803* (2013.01); *A61K 9/0019* (2013.01); *A61K 31/496* (2013.01); *A61K 39/395* (2013.01); *A61P 35/02* (2018.01)

(58) Field of Classification Search
None
See application file for complete search history.

(56) References Cited

U.S. PATENT DOCUMENTS

| 4,708,871 | A | 11/1987 | Geysen | 424/88 |
| 5,686,072 | A | 11/1997 | Uhr et al. | 424/183.1 |
| 7,109,304 | B2 | 9/2006 | Hansen et al. | 530/387.3 |
| 7,514,444 | B2 | 4/2009 | Honigberg et al. | 514/263.22 |
| 7,902,338 | B2 | 3/2011 | Hansen et al. | 530/387.1 |
| 7,968,687 | B2 | 6/2011 | McDonagh et al. | 530/387.3 |
| 8,063,187 | B2 * | 11/2011 | Chu | A61P 3/10 530/387.1 |
| 8,097,703 | B2 | 1/2012 | Rao-Naik et al. | 530/387.1 |
| 8,323,653 | B2 | 12/2012 | Damschroder et al. | 424/144.1 |
| 8,524,867 | B2 | 9/2013 | Bernett et al. | 530/387.1 |
| 8,546,399 | B2 | 10/2013 | Bruncko et al. | 514/252.18 |
| 8,549,399 | B2 | 10/2013 | Bruncko et al. | 514/252.18 |
| 8,679,492 | B2 | 3/2014 | Blein et al. | 424/133.1 |
| 8,691,952 | B2 | 4/2014 | Super et al. | 530/387.1 |
| 8,754,090 | B2 | 6/2014 | Buggy et al. | 514/262.1 |
| 9,174,982 | B2 | 11/2015 | Bruncko et al. | C07D 471/04 |
| 10,617,691 | B2 | 4/2020 | Endell et al. | A61K 31/519 |
| 2007/0154473 | A1 | 7/2007 | Super et al. | 424/133.1 |
| 2010/0068136 | A1 | 3/2010 | Hansen et al. | 424/1.49 |
| 2010/0128586 | A1 | 5/2010 | Wu et al. | 424/1.65 |
| 2012/0128586 | A1 | 5/2012 | Calissano et al. | 424/1.65 |
| 2015/0158846 | A1 * | 6/2015 | Crawford | A61P 17/06 424/133.1 |
| 2015/0283178 | A1 * | 10/2015 | June | A61K 31/53 424/85.2 |
| 2017/0137516 | A1 | 5/2017 | Foster et al. | C07K 16/2803 |
| 2018/0153892 | A1 | 6/2018 | Endell et al. | A61K 31/519 |
| 2019/0195879 | A1 | 6/2019 | Endell et al. | G01N 33/57426 |
| 2021/0130461 | A1 | 5/2021 | Endell et al. | C07K 16/2803 |
| 2021/0154209 | A1 | 5/2021 | Baskin-Bay et al. | A61K 31/573 |
| 2021/0292410 | A1 | 9/2021 | Kelemen et al. | C07K 16/2803 |

FOREIGN PATENT DOCUMENTS

| CN | 103703027 | 4/2014 |
| CN | 103732252 | 4/2014 |
| CN | 109890418 | 6/2019 |
| JP | 2014525925 | 10/2014 |
| JP | 2014525926 | 10/2014 |
| WO | 2002/022212 | 3/2002 |
| WO | WO 2003/048731 | 6/2003 |
| WO | 2005/012493 | 2/2005 |
| WO | 2007/002223 | 1/2007 |
| WO | 2007/076950 | 7/2007 |

(Continued)

OTHER PUBLICATIONS

Anderson et al. "Expression of Human B cell—Associated Antigens on Leukemias and Lymphomas: A Model of Human B Cell Differentiation" Blood 1984 63:1424-1433.

Grossbard et al. "Anti-B4-blocked ricin: a phase II trial of 7 day continuous infusion in patients with multiple myeloma" Br. J. Haematol 1998 102:509-515.

Kalos et al. "T cells with Chimeric Antigen Receptors Have Potent Antitumor Effects and Can Establish Memory in Patients with Advanced Leukemia" Science Translational Medicine 2011 3(95):1-21.

Karlsson et al. "Combining CAR T cells and the Bcl-2 family apoptosis inhibitor ABT-737 for treating B-cell malignancy" Cancer Gene Therapy 2013 20:386-393.

(Continued)

*Primary Examiner* — Yunsoo Kim
(74) *Attorney, Agent, or Firm* — Fish & Richardson P.C.

(57) ABSTRACT

The present disclosure describes a pharmaceutical combination of an anti-CD19 antibody and a BCL-2 inhibitor for the treatment of non-Hodgkin's lymphoma, chronic lymphocytic leukemia and/or acute lymphoblastic leukemia.

20 Claims, 10 Drawing Sheets
Specification includes a Sequence Listing.

(56) References Cited

FOREIGN PATENT DOCUMENTS

| WO | 2008/022125 | 2/2008 |
|---|---|---|
| WO | WO 2008/022152 | 2/2008 |
| WO | 2008/031056 | 3/2008 |
| WO | 2008/150494 | 12/2008 |
| WO | 2009/052431 | 4/2009 |
| WO | 2010/053716 | 5/2010 |
| WO | 2010/095031 | 8/2010 |
| WO | 2010/151341 | 12/2010 |
| WO | 2011/147834 | 12/2011 |
| WO | 2012/010561 | 1/2012 |
| WO | 2012/010562 | 1/2012 |
| WO | 2012/156455 | 11/2012 |
| WO | 2013/024095 | 2/2013 |
| WO | 2013/024097 | 2/2013 |
| WO | 2015/130585 | 9/2015 |
| WO | WO 2015/195498 | 12/2015 |
| WO | WO 2016/064929 | 4/2016 |
| WO | 2016/130902 | 8/2016 |
| WO | WO 2016/188935 | 12/2016 |
| WO | WO 2016/189014 | 12/2016 |
| WO | WO 2017/004532 | 1/2017 |
| WO | WO 2017/032679 | 3/2017 |
| WO | WO 2017/207574 | 12/2017 |
| WO | WO 2018/002031 | 1/2018 |
| WO | WO 2018/220040 | 12/2018 |
| WO | WO 2019/113301 | 6/2019 |
| WO | WO 2020/055040 | 3/2020 |
| WO | WO 2020/225196 | 11/2020 |
| WO | WO 2021/084062 | 5/2021 |
| WO | WO 2021/084063 | 5/2021 |
| WO | WO 2021/084064 | 5/2021 |
| WO | WO 2021/259902 | 12/2021 |
| WO | WO 2022/117799 | 6/2022 |
| WO | WO 2023/118395 | 6/2023 |

OTHER PUBLICATIONS

Loken et al. "Flow Cyotmetric Analysis of Human Bone Marrow: I. Normal Erythroid Development" Blood 1987 70:1316-1324.
Nadler et al. "B4, A Human B Lymphocyte—associated Antigen Expressed on Normal Mitogen-Activated, and Malignant B Lymphocytes" J. Immunol. 1983 131:244-250.
Sadelain et al. :The promise and potential pitfalls of chimeric antigen receptors Current Opinion in Immunology 2009 21(2):215-223.
Scheuermann et al. "CD19 Antigen in Leukemia and Lymphoma Diagnosis and Immunotherapy" Leukemia and Lymphoma 1995 18:385-397.
Treon et al. "Expression of Serotherapy Target Antigens in Waldenstrom's Macroglobulinemia: Therapeutic Applications and Considerations" Semin. Oncol 2003 30:248-52.
Uckun et al. "Detailed Studies on Expression and Function of CD19 Surface Determinant by Using B43 Monoclonal Antibody and the Clinical Potential of Anti-CD19 Immunotoxins" Blood, 1988 71:13-29.
Extended European Search Report in EP 16196184.2 dated Sep. 14, 2017.
Caruana et al., "From Monoclonal Antibodies to Chimeric Antigen Receptors for the Treatment of Human Malignancies," Semin Oncol., Oct. 2014, 41(5):661-666.
Chou et al., "Quantitative analysis of dose-effect relationships: the combined effects of multiple drugs or enzyme inhibitors," Adv Enzyme Regul., 1984, 22:27-55.
Chou, "Theoretical Basis, Experimental Design, and Computerized Simulation of Synergism and Antagonism in Drug Combination Studies," Pharmacol Rev., 2006, 58:621-681.
Clarke, "Issues in experimental design and endpoint analysis in the study of experimental cytotoxic agents in vivo in breast cancer and other models," Breast Cancer Research and Treatment, 1997, 46:255-278.

Geysen et al., "A priori delineation of a peptide which mimics a discontinuous antigenic determinant," Mol. Immunol., 1986, 23:709-715.
Geysen et al., "Small peptides induce antibodies with a sequence and structural requirement for binding antigen comparable to antibodies raised against the native protein," Proc Natl Acad Sci USA., 1985, 82:178-182.
Geysen et al., "Use of peptide synthesis to probe viral antigens for epitopes to a resolution of a single amino acid," Proc Natl Acad Sci USA., 1984, 8:3998-4002.
Hopp et al., "Prediction of protein antigenic determinants from amino acid sequences," Proc Natl Acad Sci USA., 1981, 78:3824-3828.
Imgt.org, "Human IGH C-REGIONs," Jun. 16, 2020 [retrieved on Jan. 12, 2021], retrieved from URL <www.imgt.org/IMGTrepertoire/Proteins/protein/human/IGH/IGHC/Hu_IGHCallgen es.html>, 2 pages.
International Preliminary Report on Patentability in International Application No. PCT/EP2017/077654, dated Apr. 30, 2019, 6 pages.
Jin et al., "Monoclonal antibodies and chimeric antigen receptor (CAR) T cells in the treatment of colorectal cancer," Cancer Cell Int., 2021, 21:83.
Kyte et al., "A simple method for displaying the hydropathic character of a protein," J Mol Biol., 1982, 157:105-132.
Loken et al., "Flow Cytometric Analysis of Human Bone Marrow: I. Normal Erythroid Development," Blood, Jan. 1987, 69(1):255-263.
Ma, "Deep and Durable Responses Following Venetoclax (ABT-199 / GDC-0199) Combined with Rituximab in Patients with Relapsed/Refractory Chronic Lymphocytic Leukemia: Results from a Phase 1b Study," Blood, Dec. 3, 2015, 126(23):830.
Robak et al., "Antibody therapy alone and in combination with targeted drugs in chronic lymphocytic leukemia," Semin Oncol., Apr. 2016, 43(2):280-290.
Abou Zahr et al., "Pharmacotherapy of relapsed/refractory chronic lymphocytic leukemia," Expert opinion on pharmacotherapy, 2017, 18(9):857-873.
Boxhammer et al., "Activity of The CD19 AntibodyMOR208 in Combination with Ibrutinib, Idelalisib or Venetoclax in Vitro," EHA Learning Center, 2017, pp. 1-2.
Campo et al., "The 2008 WHO classification of lymphoid neoplasms and beyond: evolving concepts and practical applications," Blood, 2011, 117(19):5019-5032.
ClinicalTrials.gov [online], "History of Changes for Study: NCT02639910 Study to Evaluate Efficacy and Safety of MOR208 With Idelalisib or Venetoclax in R/R CLL/SLL Patients Pretreated With BTK," NCT02639910, Submitted on May 19, 2017, Apr. 27, 2023, https://clinicaltrials.gov/ct2/history/NCT02639910?V_7=View#StudyPageTop, 7 pages.
Clinicaltrials.gov, "A Phase II, Two-Cohort, Open-Label, Multicenter Study to Evaluate the Efficacy and Safety of MOR00208 Combined with Idelalisib or Venetoclax in Patients With Relapsed or Refractory CLL/SLL Previously Treated with Bruton's Tyrosine Kinase(BTK) Inhibitor," NCT02639910, last updated May 21, 2017, pp. 1-4.
Clinicaltrials.gov, "Bcl-2 Inhibitor GDC-0199 in Combination With Obinutuzumab and Ibrutinib in Treating Patients With Relapsed, Refractory, or Previously Untreated Chronic Lymphocytic Leukemia," NCT02427451, last updated on Nov. 17, 2022, 15 pages.
Dores et al., "Chronic lymphocytic leukaemia and small lymphocytic lymphoma: overview of the descriptive epidemiology," 2007, 139(5):809-819.
Extended European Search Report for the Application No. 17173712.5, dated Oct. 4, 2017, 8 pages.
Fischer et al., "Results of the safety run-in phase of CLL14 (BO25323): a prospective, open-label, multicenter randomized phase III trial to compare the efficacy and safety of obinutuzumab and venetoclax (GDC-0199/ABT-199) with obinutuzumab and chlorambucil in patients with previously untreated CLL and coexisting medical conditions," Blood, 2015, 126(23):496.
Fischer et al., "Safety and Efficacy of Venetoclax and Obinutuzumab in Patients with Previously Untreated Chronic Lymphocytic Leukemia (CLL) and Coexisting Medical Conditions: Final Results of

(56) References Cited

OTHER PUBLICATIONS the Run-in Phase of the Randomized CLL14 Trial (BO25323)," Blood, Dec. 2016, 128(22):2054.

Hallek et al., "Guidelines for the diagnosis and treatment of chronic lymphocytic leukemia: a report from the International Workshop on Chronic Lymphocytic Leukemia updating the National Cancer Institute-Working Group 1996 guidelines," Blood, 2008, 111(12): 5446-5456.

International Preliminary Report on Patentability in International Application No. PCT/EP2018/064229, dated Dec. 3, 2019, 8 pages.

International Search Report and Written Opinion in International Application No. PCT/EP2018/064229, dated Apr. 9, 2018, 12 pages.

Jagasia et al., "Complications of hematopoietic neoplasms," Wintrobe's Clinical Hematology, 11th edition, 2003, 2(72):1919-1944.

Martens et al., "CD3xCD19 DART molecule treatment induces non-apoptotic killing and is efficient against high-risk chemotherapy and venetoclax-resistant chronic lymphocytic leukemia cells," J Immunother Cancer., 2020, 8:e000218.

Morabito et al., "Promising therapies for the treatment of chronic lymphocytic leukemia," Expert Opinion on Investigational Drugs, 2015, 24(6):795-807.

Shah et al., "Incorporating Novel Targeted and Immunotherapeutic Agents in the Treatment of B-Cell Lymphomas," Hematologic Malignancies, Mar. 25, 2021, pp. 310-327.

Wendtner et al., "Cosmos: MOR208 plus idelalisib or venetoclax in patients with relapsed or refractory (R/R) chronic lymphocytic leukemia (CLL) or small lymphocytic lymphoma (SLL) previously treated with a Bruton's tyrosine kinase inhibitor (BTKi)—a two-cohort phase II study," ASCO 2017, Jun. 6, 2017, Poster Abstract TPS7567, 3 pages.

Yang et al., "Insights Into Immunothrombosis: The Interplay Among Neutrophil Extracellular Trap, von Willebrand Factor, and ADAMTS13," Frontiers In Immunol., Dec. 2020, 11:610696.

Office Communication in U.S. Appl. No. 16/615,953, filed Nov. 22, 2019 dated Nov. 26, 2021.

Office Communication in U.S. Appl. No. 16/615,953, filed Nov. 22, 2019 dated Apr. 22, 2022.

Office Communication in U.S. Appl. No. 16/615,953, filed Nov. 22, 2019 dated Aug. 29, 2022.

Office Communication in U.S. Appl. No. 16/615,953, filed Nov. 22, 2019 dated Nov. 9, 2022.

Ishioka, "Carcinogenesis and apoptosis of cell," Japanese Journal of Clinical Medicine, Jan. 2009, 67(S1):77-85 (with machine english abstract).

Naoe et al., "Molecule-targeted therapy for malignant lymphoma," History of Medicine, Jan. 2005, 212(5):383-388 (with machine english abstract).

Office Communication in U.S. Appl. No. 16/615,953, filed Nov. 22, 2019 dated Sep. 8, 2023.

Office Communication dated Jan. 25, 2024 in U.S. Appl. No. 16/615,953, filed Nov. 22, 2019.

Abb Vie Inc., "Venclexta Prescribing Information," 2016, retrieved from URL<https://www.accessdata.fda.gov/drugsatfda_docs/label/2016/208573s0001bl.pdf>, 25 pages.

Extended European Search Report in European Application No. 23190328.7, dated Feb. 5, 2024, 11 pages.

Kang et al., "Bcl-2 Inhibitors: Targeting Mitochondrial Apoptotic Pathways in Cancer Therapy," Clinical Cancer Research, 2009, 15(4):1126-1132.

Staber et al., "Primary Analysis of Anti-CD19 Tafasitamab (MOR208) Treatment in Combination with Idelalisib or Venetoclax in R/R Cll Patients Who Failed Prior BTK Inhibitor Therapy (COSMOS Trial)," Blood, 2019, 134(Suppln. 1):1754, 5 pages.

Horton et al., "Potent in vitro and in vivo activity of an Fc-engineered anti-CD19 monoclonal antibody against lymphoma and leukemia," Cancer Research, Oct. 1, 2008, 68(19):8049-8057.

\* cited by examiner

Cytotoxicity of MOR00208 and venetoclax in combination in MEC-1 cell line

Cytotoxicity of MOR00208 and venetoclax in combination in MEC-1 cell line

Figure 4

The amino acid sequence of the MOR00208 Variable Heavy Domain is:
(The CDRs are bolded and underlined)

EVQLVESGGGLVKPGGSLKLSCAASGYTFTSYVMHWVRQAPGKGLEWIGYINPYNDGTKYNEKFQGRVTISSDKSISTAYMELSSLRSEDTAMYYCARGTYYYGTRVFDYWGQGTLVTVSS (SEQ ID NO: 10)

The amino acid sequence of the MOR00208 Variable Light Domain is:
(The CDRs are bolded and underlined)

DIVMTQSPATLSLSPGERATLSCRSSKSLQNVNGNTYLYWFQQKPGQSPQLLIYRMSNLNSGVPDRFSGSGSGTEFTLTISSLEPEDFAVYYCMQHLEYPITFGAGTKLEIK (SEQ ID NO: 11)

The amino acid sequence of the MOR00208 HCDR1 is: SYVMH (SEQ ID NO: 1)

The amino acid sequence of the MOR00208 HCDR2 is: NPYNDG (SEQ ID NO: 2)

The amino acid sequence of the MOR00208 HCDR3 is: GTYYYGTRVFDY (SEQ ID NO: 3)

The amino acid sequence of the MOR00208 LCDR1 is: RSSKSLQNVNGNTYLY (SEQ ID NO: 4)

The amino acid sequence of the MOR00208 LCDR2 is: RMSNLNS (SEQ ID NO: 5)

The amino acid sequence of the MOR00208 LCDR3 is: MQHLEYPIT (SEQ ID NO: 6)

Figure 5

Sequence of Fc regions

The amino acids sequence of the MOR00208 heavy chain Fc region is:

ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGG
PDVFLFPPKPKDTLMISRTPEVTCVVVDVSHEDPEVQFNWYVDGVEVHNAKTKPREEQF
NSTFRVVSVLTVVHQDWLNGKEYKCKVSNKALPAPEEKTISKTKGQPREPQVYTLPPSRE
EMTKNQVSLTCLVKGFYPSDIAVEWESNGQPENNYKTTPPMLDSDGSFFLYSKLTVDKSR
WQQGNVFSCSVMHEALHNHYTQKSLSLSPGK (SEQ ID NO: 12).

The amino acids sequence of the MOR00208 light chain Fc region is:

RTVAAPSVFIFPPSDEQLKSGTASVVCLLNNFYPREAKVQWKVDNALQSGNSQESVTEQ
DSKD STYSLSSTLTLSKADYEKHKVYACEVTHQGLSSPVTKSFNRGEC (SEQ ID NO: 13)

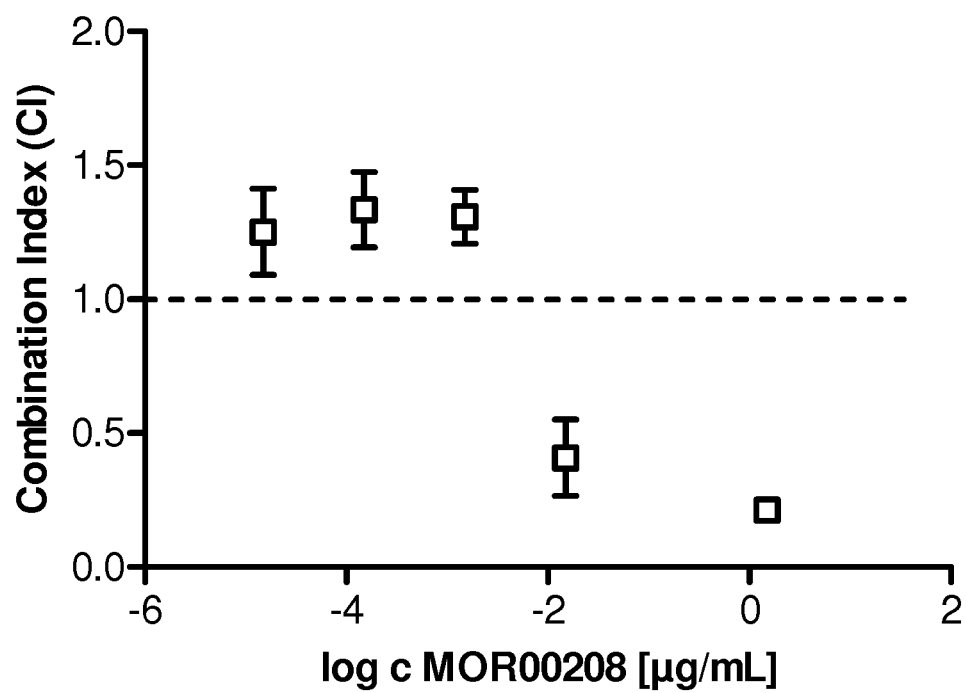

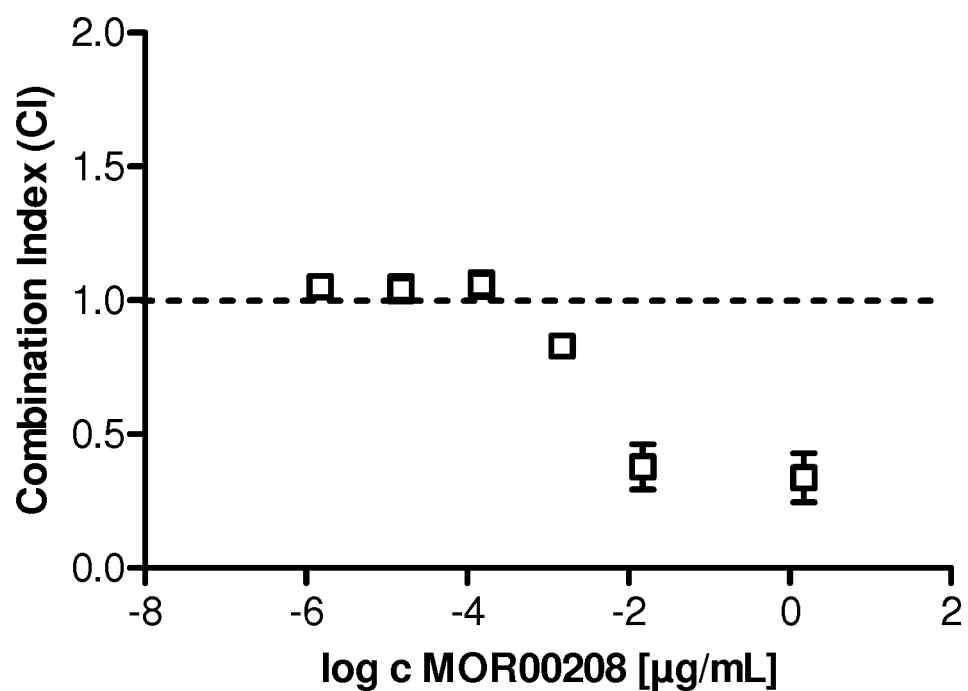

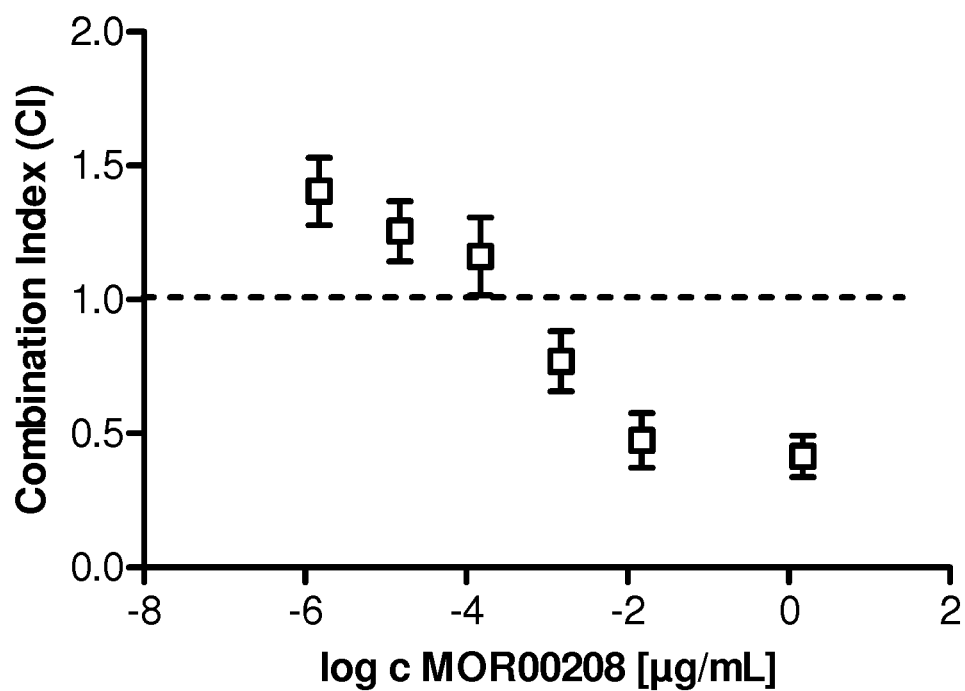

COMBINATION OF ANTI CD19 ANTIBODY WITH A BCL-2 INHIBITOR AND USES THEREOF

This patent application is the National Stage of International Application No. PCT/EP2017/077654 filed Oct. 27, 2017, which claims the benefit of EP 16196184.2 filed Oct. 28, 2016, each of which is incorporated by reference in its entirety.

FIELD OF THE INVENTION

The present disclosure is related to a pharmaceutical combination of an anti-CD19 antibody and a BCL-2 inhibitor for the treatment of non-Hodgkin's lymphoma, chronic lymphocytic leukemia and/or acute lymphoblastic leukemia.

BACKGROUND

B cells are lymphocytes that play a large role in the humoral immune response. They are produced in the bone marrow of most mammals, and represent 5-15% of the circulating lymphoid pool. The principal function of B cells is to make antibodies against various antigens, and are an essential component of the adaptive immune system.

Because of their critical role in regulating the immune system, disregulation of B cells is associated with a variety of disorders, such as lymphomas, and leukemias. These include non-Hodgkin's lymphoma (NHL), chronic lymphocytic leukemia (CLL) and acute lymphoblastic leukemia (ALL).

NHL is a heterogeneous malignancy originating from lymphocytes. In the United States (U.S.), the incidence is estimated at 65,000/year with mortality of approximately 20,000 (American Cancer Society, 2006; and SEER Cancer Statistics Review). The disease can occur in all ages, the usual onset begins in adults over 40 years, with the incidence increasing with age. NHL is characterized by a clonal proliferation of lymphocytes that accumulate in the lymph nodes, blood, bone marrow and spleen, although any major organ may be involved. The current classification system used by pathologists and clinicians is the World Health Organization (WHO) Classification of Tumours, which organizes NHL into precursor and mature B-cell or T-cell neoplasms. The PDQ is currently dividing NHL as indolent or aggressive for entry into clinical trials. The indolent NHL group is comprised primarily of follicular subtypes, small lymphocytic lymphoma, MALT (mucosa-associated lymphoid tissue), and marginal zone; indolent encompasses approximately 50% of newly diagnosed B-cell NHL patients. Aggressive NHL includes patients with histologic diagnoses of primarily diffuse large B cell (DLBL, DLBCL, or DLCL) (40% of all newly diagnosed patients have diffuse large cell), Burkitt's, and mantle cell. The clinical course of NHL is highly variable. A major determinant of clinical course is the histologic subtype. Most indolent types of NHL are considered to be incurable disease. Patients respond initially to either chemotherapy or antibody therapy and most will relapse. Studies to date have not demonstrated an improvement in survival with early intervention. In asymptomatic patients, it is acceptable to "watch and wait" until the patient becomes symptomatic or the disease pace appears to be accelerating. Over time, the disease may transform to a more aggressive histology. The median survival is 8 to 10 years, and indolent patients often receive 3 or more treatments during the treatment phase of their disease. Initial treatment of the symptomatic indolent NHL patient historically has been combination chemotherapy. The most commonly used agents include: cyclophosphamide, vincristine and prednisone (CVP); or cyclophosphamide, adriamycin, vincristine, prednisone (CHOP). Approximately 70% to 80% of patients will respond to their initial chemotherapy, duration of remissions last on the order of 2-3 years. Ultimately, the majority of patients relapse. The discovery and clinical use of the anti-CD20 antibody, rituximab, has provided significant improvements in response and survival rate. The current standard of care for most patients is rituximab+CHOP (R-CHOP) or rituximab+CVP (R-CVP). Interferon is approved for initial treatment of NHL in combination with alkylating agents, but has limited use in the U.S. Rituximab therapy has been shown to be efficacious in several types of NHL, and is currently approved as a first line treatment for both indolent (follicular lymphoma) and aggressive NHL (diffuse large B cell lymphoma). However, there are significant limitations of anti-CD20 monoclonal antibody (mAb), including primary resistance (50% response in relapsed indolent patients), acquired resistance (50% response rate upon re-treatment), rare complete response (2% complete resonse rate in relapsed population), and a continued pattern of relapse. Finally, many B cells do not express CD20, and thus many B-cell disorders are not treatable using anti-CD20 antibody therapy.

In addition to NHL there are several types of leukemias that result from disregulation of B cells. Chronic lymphocytic leukemia (also known as "chronic lymphoid leukemia" or "CLL"), is a type of adult leukemia caused by an abnormal accumulation of B lymphocytes. In CLL, the malignant lymphocytes may look normal and mature, but they are not able to cope effectively with infection. CLL is the most common form of leukemia in adults. Men are twice as likely to develop CLL as women. However, the key risk factor is age. Over 75% of new cases are diagnosed in patients over age 50. More than 10,000 cases are diagnosed every year and the mortality is almost 5,000 a year (American Cancer Society, 2006; and SEER Cancer Statistics Review). CLL is an incurable disease but progresses slowly in most cases. Many people with CLL lead normal and active lives for many years. Because of its slow onset, early-stage CLL is generally not treated since it is believed that early CLL intervention does not improve survival time or quality of life. Instead, the condition is monitored over time. Initial CLL treatments vary depending on the exact diagnosis and the progression of the disease. There are dozens of agents used for CLL therapy. Combination chemotherapy regimens such as FCR (fludarabine, cyclophosphamide and rituximab), and BR (Ibrutinib and rituximab) are effective in both newly-diagnosed and relapsed CLL. Allogeneic bone marrow (stem cell) transplantation is rarely used as a first-line treatment for CLL due to its risk.

Another type of leukemia is acute lymphoblastic leukemia (ALL), also known as acute lymphocytic leukemia. ALL is characterised by the overproduction and continuous multiplication of malignant and immature white blood cells (also known as lymphoblasts) in the bone marrow. 'Acute' refers to the undifferentiated, immature state of the circulating lymphocytes ("blasts"), and that the disease progresses rapidly with life expectancy of weeks to months if left untreated. ALL is most common in childhood with a peak incidence of 4-5 years of age. Children of age 12-16 die more easily from it than others. Currently, at least 80% of childhood ALL are considered curable. Under 4,000 cases are diagnosed every year and the mortality is almost 1,500 a year (American Cancer Society, 2006; and SEER Cancer Statistics Review).

The human CD19 molecule is a structurally distinct cell surface receptor expressed on the surface of human B cells, including, but not limited to, pre-B cells, B cells in early development {i.e., immature B cells), mature B cells through terminal differentiation into plasma cells, and malignant B cells. CD 19 is expressed by most pre-B acute lymphoblastic leukemias (ALL), non-Hodgkin's lymphomas, B cell chronic lymphocytic leukemias (CLL), pro-lymphocytic leukemias, hairy cell leukemias, common acute lymphocytic leukemias, and some Null-acute lymphoblastic leukemias (Nadler et al, J. Immunol., 131:244-250 (1983), Loken et al, Blood, 70:1316-1324 (1987), Uckun et al, Blood, 71:13-29 (1988), Anderson et al, 1984. Blood, 63:1424-1433 (1984), Scheuermann, Leuk. Lymphoma, 18:385-397(1995)). The expression of CD 19 on plasma cells further suggests it may be expressed on differentiated B cell tumors such as multiple myeloma, plasmacytomas, Waldenstrom's tumors (Grossbard et al., Br. J. Haematol, 102:509-15(1998); Treon et al, Semin. Oncol, 30:248-52 (2003)).

Therefore, the CD 19 antigen is a target for immunotherapy in the treatment of non-Hodgkin's lymphoma (including each the subtypes described herein), chronic lymphocytic leukemia and/or acute lymphoblastic leukemia.

Certain CD19 therapies have been shown. T cells expressing an anti-CD19 chimeric antigen receptor (CAR) including both CD3-4 and the 4-BB costimulatory domain were administered to patients with advanced CLL. Kalos et al., T cells with Chimeric Antigen Receptors Have Potent Antitumor Effects and Can Establish Memory in Patients with Advanced Leukemia, Science Translational Medicine, vol. 3, no. 95 (10 Aug. 2011), which is incorporated by reference in its entirety. Sadelain et al., The promise and potential pitfalls of chimeric antigen receptors, Current Opinion in Immunology, Elsevier, vol. 21, no. 2, 2 Apr. 2009, which is incorporated by reference in its entirety, also describes anti-CD19 chimeric antigen receptors (CARs). Neither Kalos et al. nor Sadelain et al., however, describe the antibody specific for CD19 in combination with a BCL-2 inhibitor as exemplified herein.

The use of a CD19 antibody in non-specific B cell lymphomas is discussed in WO2007076950 (US2007154473), which are both incorporated by reference in their entireties, along with the cursory mention of Ibrutinib within a long list of potential combination partners, but fails either to teach the antibody exemplified herein or suggest the synergistic effects of the combination in the treatment of non-Hodgkin's lymphoma, chronic lymphocytic leukemia and/or acute lymphoblastic leukemia as exemplified herein.

The use of a CD19 antibody in CLL, NHL and ALL is described in Scheuermann et al., CD19 Antigen in Leukemia and Lymphoma Diagnosis and Immunotherapy, Leukemia and Lymphoma, Vol. 18, 385-397 (1995), which is incorporated by reference in its entirety, but fails to suggest the combination exemplified herein.

Additional antibodies specific for CD19 are described in WO2005012493 (U.S. Pat. No. 7,109,304), WO2010053716 (U.S. Ser. No. 12/266,999) (Immunomedics); WO2007002223 (US U.S. Pat. No. 8,097,703) (Medarex); WO2008022152 (Ser. No. 12/377,251) and WO2008150494 (Xencor), WO2008031056 (U.S. Ser. No. 11/852,106) (Medimmune); WO 2007076950 (U.S. Ser. No. 11/648,505) (Merck Patent GmbH); WO 2009/052431 (U.S. Ser. No. 12/253,895) (Seattle Genetics); and WO2010095031 (Ser. No. 12/710,442) (Glenmark Pharmaceuticals), WO2012010562 and WO2012010561 (International Drug Development), WO2011147834 (Roche Glycart), and WO 2012/156455 (Sanofi), which are all incorporated by reference in their entireties.

Combinations of antibodies specific for CD19 and other agents are described in WO2010151341 (U.S. Ser. No. 13/377,514) (The Feinstein Institute); U.S. Pat. No. 5,686, 072 (University of Texas), and WO2002022212 (PCT/US01/29026) (IDEC Pharmaceuticals), WO2013/024097 (Ser. No. 14/126,928) (MorphoSys AG) and WO2013/024095 (Ser. No. 14/127,217) (MorphoSys AG), which are all incorporated by reference in their entireties.

Certain BCL-2 inhibitors are commercially available. VENCLEXTA™ (venetoclax), also known as GDC-0199, ABT-199, and RG7601 is a BCL-2 inhibitor indicated for the treatment of patients with chronic lymphocytic leukemia (CLL) with 17p deletion, as detected by an FDA approved test, who have received at least one prior therapy. Venetoclax is described in U.S. Pat. Nos. 8,546,399 and 9,174,982, which are all incorporated by reference in their entireties.

Despite the recent progress in the discovery and development of anti-cancer agents, many forms of cancer involving CD19-expressing tumors still have a poor prognosis. Thus, there is a need for improved methods for treating such forms of cancer.

SUMMARY

Neither alone nor in combination does the prior art suggest the synergistic effects of the combination of the exemplified antibody and venetoclax in the treatment of non-Hodgkin's lymphoma, chronic lymphocytic leukemia and/or acute lymphoblastic leukemia.

In one aspect, the present disclosure relates to a synergistic combination of an antibody specific for CD19 and a BCL-2 inhibitor. Such combinations are useful in the treatment of B cell malignancies, such as, non-Hodgkin's lymphoma, chronic lymphocytic leukemia and/or acute lymphoblastic leukemia.

In vitro models are considered indicative of how a certain compound or combination of compounds would behave in humans.

MEC-1 cells (DSMZ# ACC497) are a chronic B-cell leukemia cell line. MEC-1 cells in the present in vitro model are indicative of how the combination will work in the treatment of chronic lymphoid leukemia (CLL) in humans.

In addition, when compounds are combined in vitro, one expects that the combination has only additive effects. Surprisingly, the inventors found that the combination of a particular antibody specific for CD19 and venetoclax mediated a synergistic level of specific cell killing in vitro in comparison to the antibody and venetoclax alone. Specifically, the inventors found that the combination of MOR00208 and venetoclax mediated a synergistic level of specific cell killing in vitro in MEC-1 cells compared to the antibody and venetoclax alone.

In summary, the combination of the exemplified anti-CD19 antibody and venetoclax behaved synergistically in models relevant to CLL. As CLL is a B cell related disorders and CD19 is highly expressed on B-cells, the exemplified combination would have the same mechanism of action and should also behave synergistically in the treatment of other B cell related disorders, e.g. ALL and NHL.

Therefore, the combination of the exemplified antibody specific for CD19 and venetoclax should be effective in the treatment of humans in non-Hodgkin's lymphoma, chronic lymphocytic leukemia and/or acute lymphoblastic leukemia.

The expected efficacy of the combination of the antibody specific to CD19 exemplified and venetoclax will be confirmed in clinical trials.

As the mechanism of action of venetoclax and other BCL-2 inhibitors are similar, as they work by inhibiting the anti-apoptotic B-cell lymphoma-2 (Bcl-2) protein, leading to programmed cell death of cells, it is believed that synergy should also be seen when treating humans having non-Hodgkin's lymphoma, chronic lymphocytic leukemia and/or acute lymphoblastic leukemia with a combination of the exemplified anti-CD19 antibody and a BCL-2 inhibitor other than venetoclax.

As the exemplified anti-CD19 antibody and other anti-CD19 antibodies bind CD19, it is believed that synergy should also be seen when treating humans having non-Hodgkin's lymphoma, chronic lymphocytic leukemia and/or acute lymphoblastic leukemia with a combination of any anti-CD19 antibody and a BCL-2 inhibitor, e.g., venetoclax.

An aspect of the present disclosure comprises a combination wherein the antibody specific for CD19 comprises an HCDR1 region of sequence SYVMH (SEQ ID NO: 1), an HCDR2 region of sequence NPYNDG (SEQ ID NO: 2), an HCDR3 region of sequence GTYYYGTRVFDY (SEQ ID NO: 3), an LCDR1 region of sequence RSSKSLQNVNG-NTYLY (SEQ ID NO: 4), an LCDR2 region of sequence RMSNLNS (SEQ ID NO: 5), and an LCDR3 region of sequence MQHLEYPIT (SEQ ID NO: 6) and venetoclax. In embodiments, the combination is synergistic. In preferred aspects, the combination is used for the treatment of non-Hodgkin's lymphoma, chronic lymphocytic leukemia and/or acute lymphoblastic leukemia.

DESCRIPTION OF DRAWINGS

FIG. 4 shows the amino acid sequence of the variable domains of MOR00208.

FIG. 5 shows the amino acid sequence of the Fc regions of MOR00208.

FIGS. 6-8 show Chou-Talay Combination Index curves of MOR00208 and venetoclax in MEC-1 cell line.

DETAILED DESCRIPTION OF THE INVENTION

Figure 1:
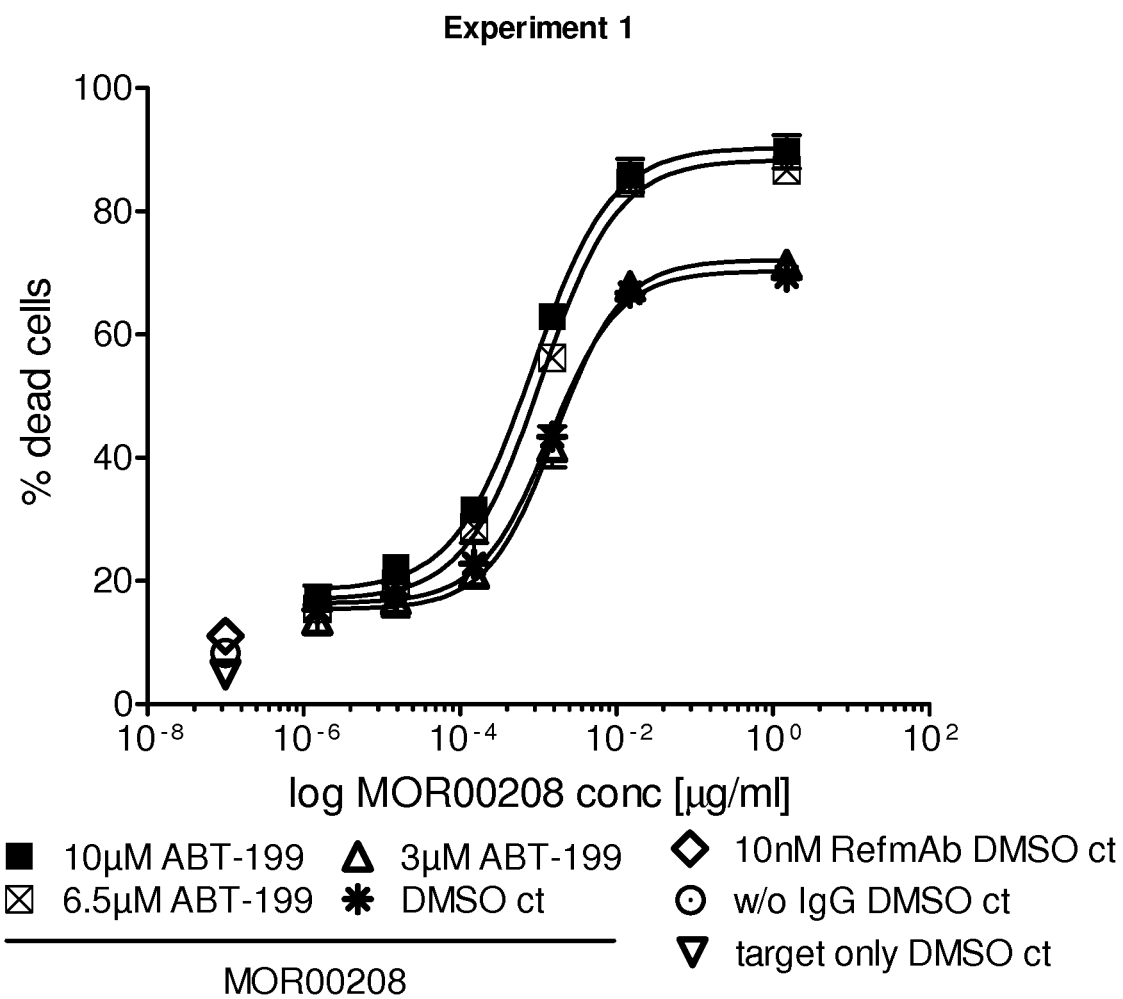
FIGS. 1-3 shows the cytotoxicity of MOR00208 and venetoclax in combination in MEC-1 cell line. MEC-1 cells were pre-treated with venetoclax for 24 hours.

"Synergy", "synergism" or "synergistic" mean more than the expected additive effect of a combination. In respect to the in vitro studies the "synergy", "synergism" or "synergistic" effect of a combination is determined herein by the methods of Chou et al., Clarke et al. and/or Webb et al. See Ting-Chao Chou, Theoretical Basis, Experimental Design, and Computerized Simulation of Synergism and Antagonism in Drug Combination Studies, Pharmacol Rev 58:621-681 (2006), which is incorporated by reference in its entirety. See also Clarke et al., Issues in experimental design and endpoint analysis in the study of experimental cytotoxic agents in vivo in breast cancer and other models, Breast Cancer Research and Treatment 46:255-278 (1997), which is incorporated by reference in its entirety. See also Webb, J. L. (1963) Enzyme and Metabolic Inhibitors, Academic Press, New York, which is incorporated by reference in its entirety.

The term "antibody" means monoclonal antibodies, including any isotype, such as, IgG, IgM, IgA, IgD and IgE. An IgG antibody is comprised of two identical heavy chains and two identical light chains that are joined by disulfide bonds. Each heavy and light chain contains a constant region and a variable region. Each variable region contains three segments called "complementarity-determining regions" ("CDRs") or "hypervariable regions", which are primarily responsible for binding an epitope of an antigen. They are referred to as CDR1, CDR2, and CDR3, numbered sequentially from the N-terminus. The more highly conserved portions of the variable regions outside of the CDRs are called the "framework regions". An "antibody fragment" means an Fv, scFv, dsFv, Fab, Fab' F(ab')2 fragment, or other fragment, which contains at least one variable heavy or variable light chain, each containing CDRs and framework regions.

Bcl-2 (B-cell lymphoma 2), encoded in humans by the BCL2 gene, is the founding member of the Bcl-2 family of regulator proteins that regulate cell death (apoptosis), by either inducing (pro-apoptotic) or inhibiting (anti-apoptotic) apoptosis. Bcl-2 is refenced by the NCBI Gene number 596. Bcl-2 is specifically considered an important anti-apoptotic protein and is thus classified as an oncogene. Bcl-2 derives its name from B-cell lymphoma 2, as it is the second member of a range of proteins initially described in chromosomal translocations involving chromosomes 14 and 18 in follicular lymphomas. Orthologs (such as Bcl2 in mice) have been identified in numerous mammals for which complete genome data are available.

A "BCL-2 inhibitor" is a class of drug that functions by inhibiting anti-apoptotic B-cell lymphoma-2 (Bcl-2) protein, leading to programmed cell death of cells. BCL-2 inhibitor include venetoclax. Venetoclax is marketed by Abbvie and Genentech (trade name VENCLEXTA™, also known as GDC-0199, ABT-199, and RG7601). Venetoclax is currently labelled for the treatment of patients with chronic lymphocytic leukemia (CLL) with 17p deletion, as detected by an FDA approved test, who have received at least one prior therapy. The formula of venetoclax is 4-(4-{[2-(4-Chlorophenyl)-4,4-dimethyl-1-cyclohexen-1-yl]methyl}-1-piperazinyl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide and has the following structure:

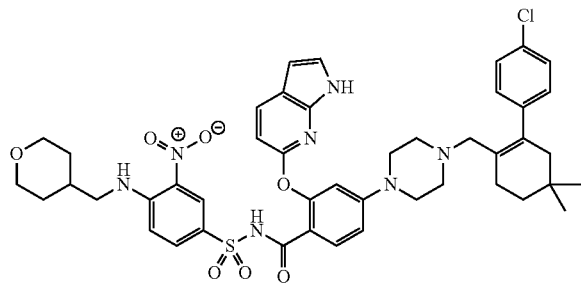 [SMILES: CC1(C)CCC(CN2CCN(c3ccc(C(=O)NS(=O)(=O)c4ccc(NCC5CCOCC5)c([N+](=O)[O-])c4)c(Oc4ccc5cc[nH]c5n4)c3)CC2)=C(c2ccc(Cl)cc2)C1]

"Venetoclax," "ABT", and "ABT-199" are used as synonyms herein.

Other BCL-2 inhibitors include:

Genasense: An antisense oligonucleotide drug Genasense (G3139) was developed by Genta Incorporated to target Bcl-2. An antisense DNA or RNA strand is non-coding and complementary to the coding strand (which is the template for producing respectively RNA or protein). An antisense drug is a short sequence of RNA that hybridises with and inactivates mRNA, preventing the protein from being formed. Human lymphoma cell proliferation (with t(14;18) translocation) could be inhibited by antisense RNA targeted at the start codon region of Bcl-2 mRNA. In vitro studies led to the identification of Genasense, which is complementary to the first 6 codons of Bcl-2 mRNA. These showed successful results in Phase I/II trials for lymphoma. A large Phase III trial was launched in 2004. As of 2016, the drug had not been approved and its developer was out of business.

ABT-737 and ABT-263: In the mid-2000s, Abbott Laboratories developed a novel inhibitor of Bcl-2, Bcl-xL and Bcl-w, known as ABT-737. This compound is part of a group of BH3 mimetic small molecule inhibitors (SMI) that target these Bcl-2 family proteins, but not A1 or Mcl-1. ABT-737 is superior to previous BCL-2 inhibitors given its higher affinity for Bcl-2, Bcl-xL and Bcl-w. In vitro studies showed that primary cells from patients with B-cell malignancies are sensitive to ABT-737. In animal models, it improves survival, causes tumor regression and cures a high percentage of mice. In preclinical studies utilizing patient xenografts, ABT-737 showed efficacy for treating lymphoma and other blood cancers. Because of its unfavorable pharmacologic properties ABT-737 is not appropriate for clinical trials, while its derivative ABT-263 has similar activity on small cell lung cancer (SCLC) cell lines and has entered clinical trials.

"VH" refers to the variable region of an immunoglobulin heavy chain of an antibody, or antibody fragment. "VL" refers to the variable region of the immunoglobulin light chain of an antibody, or antibody fragment.

The term "CD19" refers to the protein known as CD19, having the following synonyms: B4, B-lymphocyte antigen CD19, B-lymphocyte surface antigen B4, CVID3, Differentiation antigen CD19, MGC12802, and T-cell surface antigen Leu-12.

Human CD19 has the amino acid sequence of:

(SEQ ID NO: 7)
MPPPRLLFFLLFLTPMEVRPEEPLVVKVEEGDNAVLQCLKGTSDGPTQQL

TWSRESPLKPFLKLSLGLPGLGIHMRPLAIWLFIFNVSQQMGGFYLCQPG

PPSEKAWQPGWTVNVEGSGELFRWNVSDLGGLGCGLKNRSSEGPSSPSGK

-continued
LMSPKLYVWAKDRPEIWEGEPPCLPPRDSLNQSLSQDLTMAPGSTLWLSC

GVPPDSVSRGPLSWTHVHPKGPKSLLSLELKDDRPARDMWVMETGLLLPR

ATAQDAGKYYCHRGNLTMSFHLEITARPVLWHWLLRTGGWKVSAVTLAYL

IFCLCSLVGILHLQRALVLRRKRKRMTDPIRRFFKVIPPPGSGPQNQYGN

VLSLPTPTSGLGRAQRWAAGLGGTAPSYGNPSSDVQADGALGSRSPPGVG

PEEEEGEGYEEPDSEEDSEFYENDSNLGQDQLSQDGSGYENPEDEPLGPE

DEDSFSNAESYENEDEELTQPVARTMDFLSPHGSAWDPSREATSLGSQSY

EDMRGILYAAPQLRSIRGQPGPNHEEDADSYENMDNPDGPDPAWGGGGRM

GTWSTR.

"MOR00208" is an anti-CD19 antibody. The amino acid sequence of the variable domains is provided in FIG. 4. The amino acid sequence of the heavy and light chain Fc regions of MOR00208 are provided in FIG. 5. "MOR00208" and "XmAb 5574" are used as synonyms to describe the antibody shown in FIGS. 4 and 5. The MOR00208 antibody is described in U.S. patent application Ser. No. 12/377,251, which is incorporated by reference in its entirety.

U.S. patent application Ser. No. 12/377,251 describes the antibody named 4G7 H1.52 Hybrid S239D/I332E/4G7 L1.155 (later named MOR00208) as follows:

>4G7 H1.52 Hybrid S239D/I332E
(SEQ ID NO: 14)
EVQLVESGGGLVKPGGSLKLSCAASGYTFTSYVMHWVRQAPGKGLEWIGY

INPYNDGTKYNEKFQGRVTISSDKSISTAYMELSSLRSEDTAMYYCARGT

YYYGTRVFDYWGQGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLGGPDVFLFPPK

PKDTLMISRTPEVTCVVVDVSHEDPEVQFNWYVDGVEVHNAKTKPREEQF

NSTFRVVSVLTVVHQDWLNGKEYKCKVSNKALPAPEEKTISKTKGQPREP

QVYTLPPSREEMTKNQVSLTCLVKGFYPSDIAVEWESNGQPENNYKTIPP

MLDSDGSFFLYSKLTVDKSRWQQGNVFSCSVMHEALHNHYTQKSLSLSPG

K

>4G7 L1.155
(SEQ ID NO: 15)
DIVMTQSPATLSLSPGERATLSCRSSKSLQNVNGNTYLYWFQQKPGQSPQ

LLIYRMSNLNSGVPDRFSGSGSGTEFTLTISSLEPEDFAVYYCMQHLEYP

ITFGAGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

Additional antibodies specific for CD19 are described in U.S. Pat. No. 7,109,304 (Immunomedics), which is incorporated by reference in its entirety; U.S. application Ser. No. 11/917,750 (Medarex), which is incorporated by reference in its entirety; U.S. application Ser. No. 11/852,106 (Medimmune), which is incorporated by reference in its entirety; U.S. application Ser. No. 11/648,505 (Merck Patent GmbH), which is incorporated by reference in its entirety; U.S. Pat. No. 7,968,687 (Seattle Genetics), which is incorporated by reference in its entirety; and U.S. application Ser. No. 12/710,442 (Glenmark Pharmaceuticals), which is incorporated by reference in its entirety.

"Fc region" means the constant region of an antibody, which in humans may be of the IgG1, 2, 3, 4 subclass or others. The sequences of human Fc regions are available at IMGT, Human IGH C-REGIONs, www.imgt.org/IMGTrepertoire/Proteins/protein/human/IGH/IGHC/Hu_IGHCallgenes.html (retrieved on 16 May 2011).

"RefmAb33" is an antibody whose amino acid sequence is as follows:

Heavy chain including the Fc region:
(SEQ ID NO: 8)
QVTLRESGPALVKPTQTLTLTCTFSGFSLSTAGMSVGWIRQPPGKALEWL

ADIWWDDKKHYNPSLKDRLTISKDTSKNQVVLKVTNMDPADTATYYCARD

MIFNFYFDVWGQGTTVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPDVFLFPPKP

KDTLMISRTPEVICVVVDVSHEDPEVQFNWYVDGVEVHNAKTKPREEQFN

STFRVVSVLTVVHQDWLNGKEYKCKVSNKALPAPEEKTISKTKGQPREPQ

VYTLPPSREEMTKNQVSLTCLVKGFYPSDIAVEWESNGQPENNYKTTPPM

LDSDGSFFLYSKLTVDKSRWQQGNVFSCSVMHEALHNHYTQKSLSLSPG

K.

Light chain including the Fc region:
(SEQ ID NO: 9)
DIQMTQSPSTLSASVGDRVTITCSASSRVGYMHWYQQKPGKAPKLLIYDT

SKLASGVPSRFSGSGSGTEFTLTISSLQPDDFATYYCFQGSGYPFTFGGG

TKVEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC.

RefmAb33 is specific for RSV, and is used as isotype control, as it shares the same Fc region as MOR00208.

A "combination" means more than one item, e.g. a compound such as an antibody and venetoclax.

The present disclosure also relates to combinations, pharmaceuticals, and pharmaceutical compositions containing the described combinations. The two components of the combination of the present invention, e.g. the antibody specific for CD19 and venetoclax, may be administered together, simultaneously, separately or subsequently, either physically or in time.

Venetoclax is currently taken orally and is currently dosed once per day. MOR00208 is currently administered intravenously, and is currently dosed either once a week or once every two weeks.

Preferably, administration of both drugs allows for both drugs to be active in the patient at the same time. For example, if MOR208 is dosed weekly and venetoclax is dosed daily then the active substance of both drugs is present in the patient at the same time. In an embodiment, venetoclax, is administered prior to and/or separately from the administration of the antibody specific for CD19, e.g. MOR00208.

Simultaneously means that the two components are administered at a time where both components (drugs) are active in the patient at the same time. It is implied by "synergism" that both drugs are active in the patient at the same time.

Administered together can mean administered at the same time.

The components of the combination may be formulated in different pharmaceutical compositions. A pharmaceutical composition includes an active agent, eg. an antibody for therapeutic use in humans. A pharmaceutical composition may include acceptable carriers or excipients.

"Administered" or "administration" includes but is not limited to delivery by an injectable form, such as, for example, an intravenous, intramuscular, intradermal or subcutaneous route or mucosal route, for example, as a nasal spray or aerosol for inhalation or as an ingestable solution, capsule or tablet.

A "therapeutically effective amount" of a compound or combination refers to an amount sufficient to cure, alleviate or partially arrest the clinical manifestations of a given disease or disorder and its complications. The amount that is effective for a particular therapeutic purpose will depend on the severity of the disease or injury as well as on the weight and general state of the subject. It will be understood that determination of an appropriate dosage may be achieved, using routine experimentation, by constructing a matrix of values and testing different points in the matrix, all of which is within the ordinary skills of a trained physician or clinical scientist.

"Cross competes" means the ability of an antibody or other binding agent to interfere with the binding of other antibodies or binding agents to CD19 in a standard competitive binding assay. The ability or extent to which an antibody or other binding agent is able to interfere with the binding of another antibody or binding molecule to CD19, and, therefore whether it can be said to cross-compete according to the invention, can be determined using standard competition binding assays. One suitable assay involves the use of the Biacore technology (e.g. by using the BIAcore 3000 instrument (Biacore, Uppsala, Sweden)), which can measure the extent of interactions using surface plasmon resonance technology. Another assay for measuring cross-competing uses an ELISA-based approach. A high throughput process for "epitope binning" antibodies based upon their cross-competition is described in International Patent Application No. WO 2003/48731

The term "epitope" includes any protein determinant capable of specific binding to an antibody or otherwise interacting with a molecule. Epitopic determinants generally consist of chemically active surface groupings of molecules such as amino acids or carbohydrate or sugar side chains and can have specific three-dimensional structural characteristics, as well as specific charge characteristics. An epitope may be "linear" or "conformational." The term "linear epitope" refers to an epitope with all of the points of interaction between the protein and the interacting molecule (such as an antibody) occur linearally along the primary amino acid sequence of the protein (continuous). The term "conformational epitope" refers to an epitope in which discontinuous amino acids that come together in three dimensional conformation. In a conformational epitope, the points of interaction occur across amino acid residues on the protein that are separated from one another.

"Binds the same epitope as" means the ability of an antibody or other binding agent to bind to CD19 and having the same epitope as the exemplified antibody. The epitopes of the exemplified antibody and other antibodies to CD19 can be determined using standard epitope mapping techniques. Epitope mapping techniques, well known in the art. include Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al, (1984) Proc. Natl. Acad. Sci. USA 8:3998-4002; Geysen et al, (1985) Proc. Natl. Acad. Sci. USA 82:78-182; Geysen et al, (1986) Mol. Immunol. 23:709-715. Similarly, conformational epitopes are readily identified by determining spatial conformation of amino acids such as by, e.g., hydrogen/deuterium exchange, x-ray crystallography and two-dimensional nuclear magnetic resonance. See, e.g., Epitope Mapping Protocols, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al, (1981) Proc. Natl. Acad. Sci USA 78:3824-3828; for determining antigenicity profiles, and the Kyte-Doolittle technique, Kyte et al, (1982) J. Mol. Biol. 157: 105-132; for hydropathy plots.

Embodiments

An aspect of the present disclosure is a combination comprising an antibody specific for CD19 and a BCL-2 inhibitor for use in the treatment of non-Hodgkin's lymphoma, chronic lymphocytic leukemia and/or acute lymphoblastic leukemia. In embodiments, the combination is synergistic.

Herein, the combination of the exemplified anti-CD19 antibody and venetoclax behaved synergistically in in vitro models relevant to CLL. As CLL is a B cell related disorder and CD19 is highly expressed on B-cells, the exemplified combination should have the same mechanism of action and should also behave synergistically in the treatment of other B cell related disorders, e.g. ALL and NHL. Therefore, the combination of the exemplified antibody specific for CD19 and venetoclax should be effective in the treatment of humans in non-Hodgkin's lymphoma, chronic lymphocytic leukemia and/or acute lymphoblastic leukemia. The expected efficacy of the combination of the antibody specific to CD19 exemplified and venetoclax will be confirmed in clinical trials.

MEC-1 cells (DSMZ# ACC497), a chronic B-cell leukemia cell line, were tested. MEC-1 cells in the present in vitro model are indicative of how the combination will work in the treatment of chronic lymphoid leukemia (CLL) in humans. The Chou index values indicate clear synergism of the combination of MOR00208 and venetoclax in the specific killing of MEC-1 cells as compared to MOR00208 and venetoclax alone.

In summary, the combination of the exemplified anti-CD19 antibody and venetoclax behaved synergistically in models relevant to CLL.

Therefore, the combination of the exemplified antibody specific for CD19 and venetoclax should be effective in the treatment of humans in non-Hodgkin's lymphoma, chronic lymphocytic leukemia and/or acute lymphoblastic leukemia.

As the mechanism of action of venetoclax and other BCL-2 inhibitors are similar, it is believed that synergy should also be seen when treating humans having non-Hodgkin's lymphoma, chronic lymphocytic leukemia and/or acute lymphoblastic leukemia with a combination of the exemplified anti-CD19 antibody and a BCL-2 inhibitor other than venetoclax.

As the exemplified anti-CD19 antibody and other anti-CD19 antibodies bind CD19, it is believed that synergy should also be seen when treating humans having non-Hodgkin's lymphoma, chronic lymphocytic leukemia and/or acute lymphoblastic leukemia with a combination of any anti-CD19 antibody and a B-cell lymphoma-2 (Bcl-2) protein inhibitor, where the anti-CD19 antibody is, for example, described in U.S. patent application Ser. No. 12/377,251 (Xencor), WO2005012493, WO2010053716 (Immunomedics); WO2007002223 (Medarex); WO2008022152 (Xencor); WO2008031056 (Medimmune); WO 2007/076950 (Merck Patent GmbH); WO 2009/052431 (Seattle Genetics); and WO2010095031 (Glenmark Pharmaceuticals), all of which are incorporated by reference in their entireties.

In embodiments, the antibody specific for CD19 comprises an antibody that cross-competes with the antibody comprising an HCDR1 region of sequence SYVMH (SEQ ID NO: 1), an HCDR2 region of sequence NPYNDG (SEQ ID NO: 2), an HCDR3 region of sequence GTYYYGTRVFDY (SEQ ID NO: 3), an LCDR1 region of sequence RSSKSLQNVNGNTYLY (SEQ ID NO: 4), an LCDR2 region of sequence RMSNLNS (SEQ ID NO: 5), and an LCDR3 region of sequence MQHLEYPIT (SEQ ID NO: 6).

In embodiments, the antibody specific for CD19 comprises an antibody that binds to the same epitope as an antibody comprising an HCDR1 region of sequence SYVMH (SEQ ID NO: 1), an HCDR2 region of sequence NPYNDG (SEQ ID NO: 2), an HCDR3 region of sequence GTYYYGTRVFDY (SEQ ID NO: 3), an LCDR1 region of sequence RSSKSLQNVNGNTYLY (SEQ ID NO: 4), an LCDR2 region of sequence RMSNLNS (SEQ ID NO: 5), and an LCDR3 region of sequence MQHLEYPIT (SEQ ID NO: 6).

In embodiments, the antibody specific for CD19 comprises an HCDR1 region of sequence SYVMH (SEQ ID NO: 1), an HCDR2 region of sequence NPYNDG (SEQ ID NO: 2), an HCDR3 region of sequence GTYYYGTRVFDY (SEQ ID NO: 3), an LCDR1 region of sequence RSSKSLQNVNGNTYLY (SEQ ID NO: 4), an LCDR2 region of sequence RMSNLNS (SEQ ID NO: 5), and an LCDR3 region of sequence MQHLEYPIT (SEQ ID NO: 6).

In embodiments, the antibody specific for CD19 has a cytotoxic activity. In embodiments, the antibody specific for CD19 comprises a constant region having ADCC inducing activity. In embodiments, the antibody specific for CD19 induces ADCC.

In embodiments, the antibody specific for CD19 induces ADCC and comprises an HCDR1 region of sequence SYVMH (SEQ ID NO: 1), an HCDR2 region of sequence NPYNDG (SEQ ID NO: 2), an HCDR3 region of sequence GTYYYGTRVFDY (SEQ ID NO: 3), an LCDR1 region of sequence RSSKSLQNVNGNTYLY (SEQ ID NO: 4), an LCDR2 region of sequence RMSNLNS (SEQ ID NO: 5), and an LCDR3 region of sequence MQHLEYPIT (SEQ ID NO: 6).

In embodiments, the antibody specific for CD19 comprises an HCDR1 region of sequence SYVMH (SEQ ID NO: 1), an HCDR2 region of sequence NPYNDG (SEQ ID NO: 2), an HCDR3 region of sequence GTYYYGTRVFDY (SEQ ID NO: 3), an LCDR1 region of sequence RSSKSLQNVNGNTYLY (SEQ ID NO: 4), an LCDR2 region of sequence RMSNLNS (SEQ ID NO:
  5), and an LCDR3 region of sequence MQHLEYPIT (SEQ ID NO: 6) and a constant region having ADCC inducing activity.

In embodiments, the antibody specific for CD19 comprises a variable heavy chain of the sequence EVQLVESGGGLVKPGGSLKLSCAASGYTFTSYVMHWVRQAPGKGLEWIGYINPY NDGTKYNEKFQGRVTISSDKSISTAYMELSSLRSEDTAMYYCARGTYYYGTRVFDYWG QGTLVTVSS (SEQ ID NO: 10) and a variable light chain of the sequence DIVMTQSPATLSLSPGERATLSCRSSKSLQNVNGNTYLYWFQQKPGQSPQLLIYR MSNLNSGVPDRFSGSGSGTEFTLTISSLEPEDFAVYYCMQHLEYPITFGAGTKLEIK (SEQ ID NO: 11).

In certain embodiments, said antibody comprises a heavy chain constant domain of the sequence ASTKGPSVFPLAPSSKSTSGGTAALGCLVKDYFPEPVTVSWNSGA LTSGVHTFPAVLQSSGLYSL SSVVTVPSSSLGT- QTYICNVNHKPSNTKVDKKVEPKSCDKTHTCPPCPAPEL- LGGPDVFLFPPKPK DTLMISRTPEVTCVVVDVSHEDPEVQFNWYVDGVEVHNAKTKPREEQFNSTFRVVSVLTVVHQD WLNGKEYKCKVSNKALPAPEEKTISKTKGQPREPQVYTLPPSREEMTKNQVSLTCLVKGFYPSDIA VEWESNGQPENNYKTTPPMLDSDGSFFLYSKLTVDKSRWQQGNVFSCSVMHEALHNHYTQKSL SLSPGK (SEQ ID NO: 12).

In embodiments, the antibody specific for CD19 comprises a light chain constant domain of the sequence RTVAAPSVFIFPPSDEQLKSGTASVVCLLNNFYPREAKVQWKVDNALQSGNSQESVTEQDSKD STYSLSSTLTLSKADYEKHKVYACEVTHQGLSSPVTKSFNRGEC. (SEQ ID NO: 13)

In embodiments, the BCL-2 inhibitor is venetoclax.

In embodiments, the components of the combination, the antibody specific for CD19 and venetoclax, are administered separately. In an embodiment, venetoclax is administered prior to administration of the antibody specific for CD19.

In embodiments, the components of the combination are administered at a time where both components (drugs) are active in the patient at the same time. It is implied by "synergism" that both drugs are active in the patient at the same time. In embodiments, the components of the combination are administered together, simultaneously, separately or subsequently, either physically or in time. In embodiments, the components of the combination are administered simultaneously.

In embodiments, the combination is a pharmaceutical composition. In embodiments, the composition comprises an acceptable carrier. In embodiments, the combination is administered in an effective amount.

An aspect of the present disclosure comprises an antibody specific for CD19 comprising an HCDR1 region of sequence SYVMH (SEQ ID NO: 1), an HCDR2 region of sequence NPYNDG (SEQ ID NO: 2), an HCDR3 region of sequence GTYYYGTRVFDY (SEQ ID NO: 3), an LCDR1 region of sequence RSSKSLQNVNGNTYLY (SEQ ID NO: 4), an LCDR2 region of sequence RMSNLNS (SEQ ID NO: 5), and an LCDR3 region of sequence MQHLEYPIT (SEQ ID NO: 6) for the treatment of non-Hodgkin's lymphoma, chronic lymphocytic leukemia and/or acute lymphoblastic leukemia, wherein said antibody is used in a synergistic combination with venetoclax.

An aspect of the present disclosure comprises an antibody specific for CD19 comprising an HCDR1 region of sequence SYVMH (SEQ ID NO: 1), an HCDR2 region of sequence NPYNDG (SEQ ID NO: 2), an HCDR3 region of sequence GTYYYGTRVFDY (SEQ ID NO: 3), an LCDR1 region of sequence RSSKSLQNVNGNTYLY (SEQ ID NO: 4), an LCDR2 region of sequence RMSNLNS (SEQ ID NO: 5), and an LCDR3 region of sequence MQHLEYPIT (SEQ ID NO: 6) for the treatment of non-Hodgkin's lymphoma, chronic lymphocytic leukemia and/or acute lymphoblastic leukemia, wherein said antibody is used in a combination with venetoclax. In an embodiment said antibody is administered in combination with venetoclax. In another embodiment said antibody is used in a combination with venetoclax, wherein said antibody and venetoclax are administered separately. In further embodiments, said antibody is administered prior to venetoxlax. In further embodiments venetoclax is administered prior to said antibody.

An aspect of the present disclosure comprises a synergistic combination of an antibody specific for CD19 comprising an HCDR1 region of sequence SYVMH (SEQ ID NO: 1), an HCDR2 region of sequence NPYNDG (SEQ ID NO: 2), an HCDR3 region of sequence GTYYYGTRVFDY (SEQ ID NO: 3), an LCDR1 region of sequence RSSKSLQNVNGNTYLY (SEQ ID NO: 4), an LCDR2 region of sequence RMSNLNS (SEQ ID NO: 5), and an LCDR3 region of sequence MQHLEYPIT (SEQ ID NO: 6) and venetoclax for the treatment of non-Hodgkin's lymphoma, chronic lymphocytic leukemia and/or acute lymphoblastic leukemia. In embodiments, the non-Hodgkin's lymphoma is selected from the group consisting of follicular lymphoma, small lymphocytic lymphoma, mucosa-associated lymphoid tissue, marginal zone, diffuse large B cell, Burkitt's, and mantle cell.

In embodiments, the non-Hodgkin's lymphoma is follicular lymphoma. In embodiments, the non-Hodgkin's lymphoma is small lymphocytic lymphoma. In embodiments, the non-Hodgkin's lymphoma is mucosa-associated lymphoid tissue. In embodiments, the non-Hodgkin's lymphoma is marginal zone lymphoma. In embodiments, the non-Hodgkin's lymphoma is diffuse large B cell lymphoma. In embodiments, the non-Hodgkin's lymphoma is Burkitt's lymphoma. In embodiments, the non-Hodgkin's lymphoma is mantle cell lymphoma.

In embodiments, the combination is for the treatment of chronic lymphocytic leukemia. In embodiments, the combination is for the treatment of acute lymphoblastic leukemia.

Another aspect comprises a method of treating non-Hodgkin's lymphoma, chronic lymphocytic leukemia and/or acute lymphoblastic leukemia in an individual in need thereof, which method comprises administration of an antibody specific for CD19 and a BCL-2 inhibitor. In embodiments of the method, the antibody specific for CD19 comprises an HCDR1 region of sequence SYVMH (SEQ ID NO: 1), an HCDR2 region of sequence NPYNDG (SEQ ID NO: 2), an HCDR3 region of sequence GTYYYGTRVFDY (SEQ ID NO: 3), an LCDR1 region of sequence RSSKSLQNVNGNTYLY (SEQ ID NO: 4), an LCDR2 region of sequence RMSNLNS (SEQ ID NO: 5), and an LCDR3 region of sequence MQHLEYPIT (SEQ ID NO: 6). In embodiments of the method, the antibody comprises the exemplified antibody specific for CD19. In embodiments of the method the BCL-2 inhibitor is venetoclax.

Another aspect includes a use of an antibody specific for CD19 wherein said antibody comprises an HCDR1 region of sequence SYVMH (SEQ ID NO: 1), an HCDR2 region of sequence NPYNDG (SEQ ID NO: 2), an HCDR3 region of sequence GTYYYGTRVFDY (SEQ ID NO: 3), an LCDR1 region of sequence RSSKSLQNVNGNTYLY (SEQ ID NO: 4), an LCDR2 region of sequence RMSNLNS (SEQ ID NO: 5), and an LCDR3 region of sequence MQHLEYPIT (SEQ ID NO: 6) in the manufacture of a medicament for the treatment of non-Hodgkin's lymphoma, chronic lymphocytic leukemia and/or acute lymphoblastic leukemia in synergistic combination with venetoclax.

EXAMPLES

Example 1: Cytotoxicity of MEC-1 Cells Using MOR00208 and Venetoclax Alone and in Combination Materials Cell lines tested: MEC-1 cells (DSMZ# ACC497). Culture conditions of cell lines used are according to supplier's information. Cell Medium: Iscove's Modified Dulbecco's Medium (IMDM), Invitrogen, Cat No.: 31980; RPMI1640, Invitrogen, Cat No.: 31870; GlutaMAX, Invitrogen, CAT No.: 35050; FCS: Sigma CAT No.: F7524 LOT No.: 111M3396. NKs: RPMI1640, with GlutaMAX, Invitrogen, Cat No.: 31870, 10% FCS; Biocoll: Biochrome AG CAT No.: L6115 LOT No.: 0034D; MACS NK cell isolation kit: Miltenyi Biotec CAT No.: 130-092-657 LOT No.: 5150402327; venetoclax: Selleck Chem. CAT No.: S8048 LOT No.: S804803; FCS: Sigma CAT No.: F7524 LOT No.: 111M3396; and RefmAb33 (anti-RSV) with same Fc region as MOR00208.

Methods

The cytotoxic potential of MOR00208 and venetoclax alone and in combination were tested in the MEC-1 cell line (CLL). Target cell killing is measured using the following parameters: venetoclax mono treatment at concentrations of 3 µM, 6.5 µM, and 10 µM; MOR00208 mono treatment at concentrations of 0.01 pM, 0.1 pM, 1 pM, 10 pM, 100 pM and 10 nM, and the combination treatment of the listed venetoclax and MOR00208 concentrations. The following are used as controls: RefnnAb33, NK cells alone, MEC-1 cells alone or DMSO. In the venetoclax mono groups as well as in the MOR00208+venetoclax combination groups, target cells were pretreated with venetoclax or with DMSO control for 24 hours followed by removal of the dead cells prior to the ADCC assay. A dead cell removal kit was used to remove cells killed by the cytotoxic effect of venetoclax. The dead cell removal kit was implemented to mimic the removal of dead cells that also occurs in vivo and to prevent false negative interference of the dead cells with the subsequent ADCC assay. For the ADCC assay, target cells are counted and stained using CFSE at a final concentration of 1 µg/mL. For the control group, i.e. DMSO treated target cells, the effector: target (E:T) cell ratio was adjusted to 2:1, i.e. $1 \times 10E6$/nnL effector cells (NK cells) and $5 \times 10E5$/mL target cells (MEC-1 cells). For the venetoclax mono group as well as for the MOR00208+venetoclax combination group the number of target cells was reduced according to the observed cytotoxic effects of venetoclax during the 24 hour treatment while the number of effector cells was kept constant at $1 \times 10^6$/mL. The ADCC assays were performed as follows: using 96 well plates, 100 µL of MEC-1 target cell suspension was added per well, followed by 100 µL NK effector cell suspension per well. Mixed cell suspensions were centrifuged and resuspended in 100 µL antibody containing medium or the according control solution. The antibodies were diluted in a range of 10 nM-0.01 pM (corresponds to 1.5 µg/mL-1.5 pg/mL) in medium. The ADCC assays were incubated for 2 hours in a CO2-incubator at 37° C. After 10 minutes incubation on ice, 50 µL DAPI solution was added to each well (final concentration 1 µg/mL) and incubated for additional 10 minutes on ice. The ADCC measurements were performed on a BD FACSVerse instrument. Dead target cells were identified as DAPI positive cells.

Data

Figure 2:
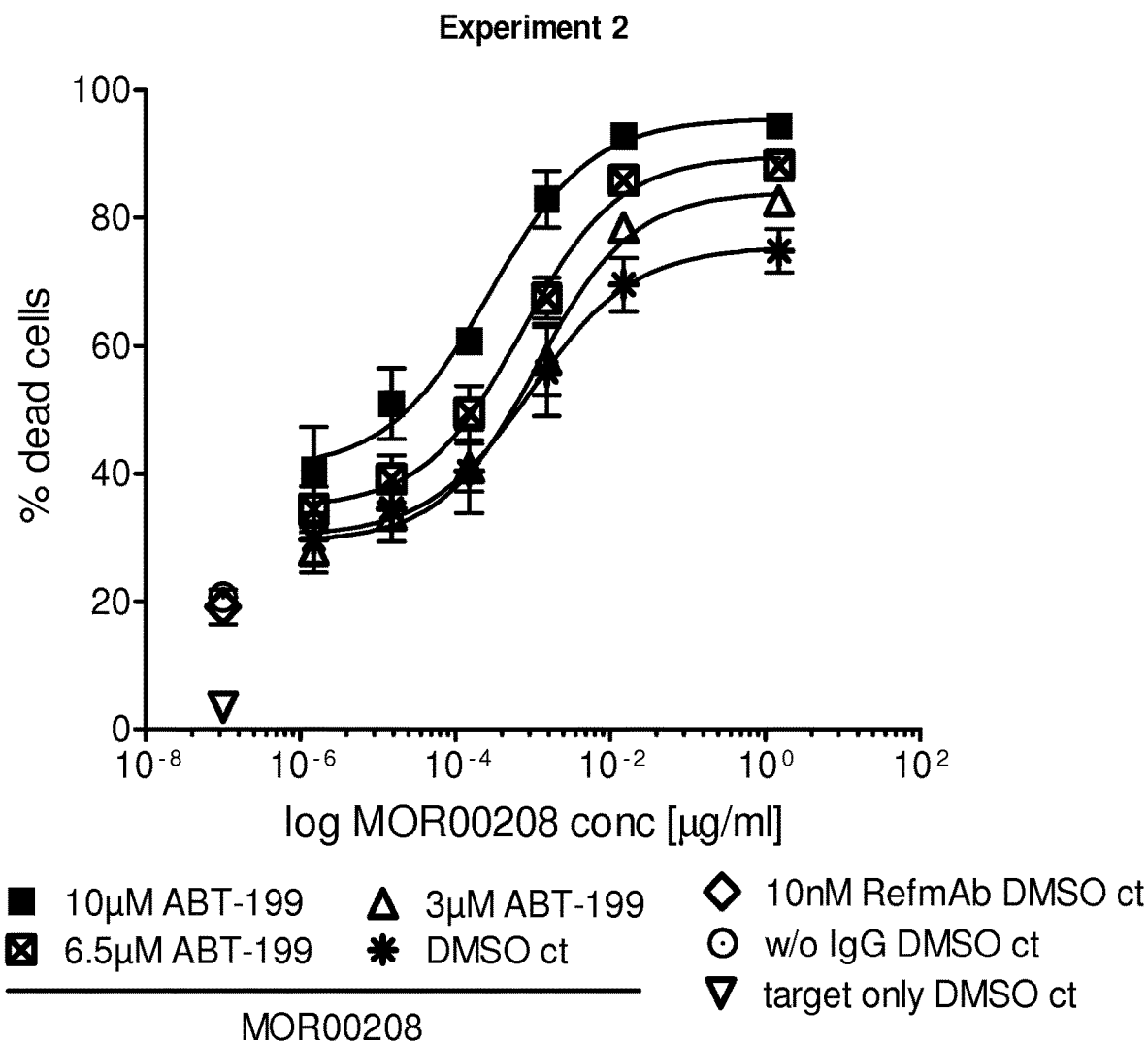
Figure 3:
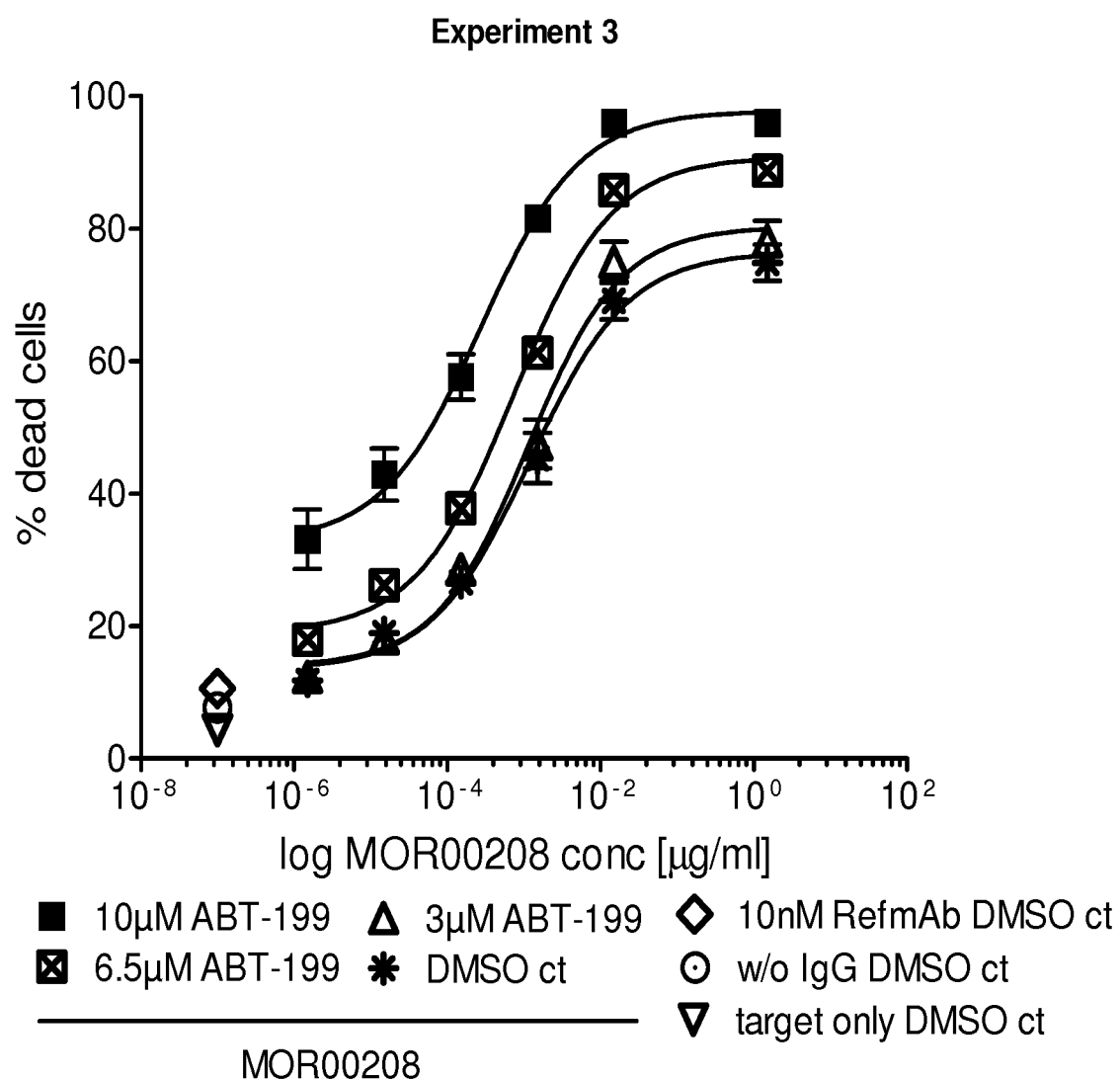

In total, three independent experiments were performed in order to determine the cytotoxic potential of the combination of MOR00208 and venetoclax. Individual raw data tables for all three experiments are shown in Tables 1-6. Individual ADCC dose response curves for all three experiments are shown in FIGS. 1-3. Mean (+/−SEM) combination index curves of all three experiments per each venetoclax concentration are shown in FIGS. 6-8.

Experiment 1:

TABLE 1

Mono activity of MOR00208 and venetoclax

| Actual MOR00208 Dose [µg/mL] | Actual MOR00208 Effect [% dead cells] |
|---|---|
| 1.50E−06 | 15.3 |
| 1.50E−05 | 17.4 |
| 1.50E−04 | 22.8 |
| 1.50E−03 | 43.4 |
| 1.50E−02 | 66.8 |
| 1.50E+00 | 69.4 |

| Actual Venetoclax Dose [µM] | Actual Venetoclax Effect [% dead cells] |
|---|---|
| 3.0 | 8.9 |
| 6.5 | 17.7 |
| 10.0 | 38.8 |

TABLE 2

Combination activity of MOR00208 and venetoclax

| Actual MOR00208 Dose [µg/mL] | Actual Venetoclax Dose [µM] | Actual MOR00208 + Venetoclax Effect [% dead cells] | Theoretical MOR00208 Dose [µg/mL] | Theoretical Venetoclax Dose [µM] | Combination Index |
|---|---|---|---|---|---|
| 1.50E−05 | 3.0 | 16.9 | 1.41E−05 | 6.3 | 1.54 |
| 1.50E−04 |  | 21.2 | 1.32E−04 | 7.2 | 1.55 |
| 1.50E−03 |  | 41.7 | 1.25E−03 | 10.4 | 1.49 |
| 1.50E−02 |  | 67.8 | 3.04E−02 | 15.1 | 0.69 |
| 1.50E+00 |  | 71.3 | * 1.00E+03 | 16.0 | 0.19 |
| 1.50E−05 | 6.5 | 19.5 | 8.47E−05 | 6.9 | 1.12 |
| 1.50E−04 |  | 28.7 | 4.10E−04 | 8.5 | 1.13 |
| 1.50E−03 |  | 56.2 | 4.04E−03 | 12.7 | 0.88 |
| 1.50E−02 |  | 84.5 | * 1.00E+03 | 21.9 | 0.30 |
| 1.50E+00 |  | 86.6 | * 1.00E+03 | 23.9 | 0.27 |
| 1.50E−06 | 10.0 | 17.3 | 2.33E−05 | 6.4 | 1.63 |
| 1.50E−05 |  | 22.1 | 1.63E−04 | 7.4 | 1.45 |

TABLE 2-continued

Combination activity of MOR00208 and venetoclax

| Actual MOR00208 Dose [μg/mL] | Actual Venetoclax Dose [μM] | Actual MOR00208 + Venetoclax Effect [% dead cells] | Theoretical MOR00208 Dose [μg/mL] | Theoretical Venetoclax Dose [μM] | Combination Index |
|---|---|---|---|---|---|
| 1.50E−04 | | 31.6 | 5.43E−04 | 8.9 | 1.40 |
| 1.50E−03 | | 62.9 | 9.14E−03 | 14.0 | 0.88 |
| 1.50E−02 | | 85.8 | * 1.00E+03 | 23.0 | 0.43 |
| 1.50E+00 | | 89.6 | * 1.00E+03 | 28.4 | 0.35 |

* Infinite theoretical MOR00208 dose as actual MOR00208 effect saturates below MOR00208 + Venetoclax effect Experiment 2:

TABLE 3

Mono activity of MOR00208 and venetoclax

| Actual MOR00208 Dose [μg/mL] | Actual MOR00208 Effect [% dead cells] |
|---|---|
| 1.50E−06 | 29.7 |
| 1.50E−05 | 34.5 |
| 1.50E−04 | 40.3 |
| 1.50E−03 | 55.9 |
| 1.50E−02 | 69.6 |
| 1.50E+00 | 74.8 |

| Actual Venetoclax Dose [μM] | Actual Venetoclax Effect [% dead cells] |
|---|---|
| 3.0 | 19.9 |
| 6.5 | 32.4 |
| 10.0 | 73.9 |

TABLE 4

Combination activity of MOR00208 and venetoclax

| Actual MOR00208 Dose [μg/mL] | Actual Venetoclax Dose [μM] | Actual MOR00208 + Venetoclax Effect [% dead cells] | Theoretical MOR00208 Dose [μg/mL] | Theoretical Venetoclax Dose [μM] | Combination Index |
|---|---|---|---|---|---|
| 1.50E−05 | 3.0 | 33.5 | 1.94E−05 | 6.6 | 1.23 |
| 1.50E−04 | | 40.9 | 1.55E−04 | 7.3 | 1.38 |
| 1.50E−03 | | 57.8 | 1.88E−03 | 8.6 | 1.15 |
| 1.50E−02 | | 78.4 | * 1.00E+03 | 10.6 | 0.28 |
| 1.50E+00 | | 82.6 | * 1.00E+03 | 11.2 | 0.27 |
| 1.50E−06 | 6.5 | 34.4 | 2.90E−05 | 6.7 | 1.02 |
| 1.50E−05 | | 39.1 | 1.09E−04 | 7.1 | 1.05 |
| 1.50E−04 | | 49.4 | 5.91E−04 | 7.9 | 1.07 |
| 1.50E−03 | | 67.4 | 1.00E−02 | 9.4 | 0.84 |
| 1.50E−02 | | 85.8 | * 1.00E+03 | 11.9 | 0.55 |
| 1.50E+00 | | 88.1 | * 1.00E+03 | 12.5 | 0.52 |
| 1.50E−06 | 10.0 | 40.5 | 1.45E−04 | 7.2 | 1.39 |
| 1.50E−05 | | 50.9 | 7.25E−04 | 8.0 | 1.26 |
| 1.50E−04 | | 60.7 | 2.89E−03 | 8.8 | 1.19 |
| 1.50E−03 | | 82.9 | * 1.00E+03 | 11.3 | 0.89 |
| 1.50E−02 | | 92.7 | * 1.00E+03 | 15.0 | 0.67 |
| 1.50E+00 | | 94.4 | * 1.00E+03 | 17.6 | 0.57 |

* Infinite theoretical MOR00208 dose as actual MOR00208 effect saturates below MOR00208 + Venetoclax effect Experiment 3:

TABLE 5

Mono activity of MOR00208 and venetoclax

| Actual MOR00208 Dose [µg/mL] | Actual MOR00208 Effect [% dead cells] |
|---|---|
| 1.50E−06 | 11.8 |
| 1.50E−05 | 18.9 |
| 1.50E−04 | 26.6 |
| 1.50E−03 | 45.3 |
| 1.50E−02 | 69.1 |
| 1.50E+00 | 74.8 |

| Actual Venetoclax Dose [µM] | Actual Venetoclax Effect [% dead cells] |
|---|---|
| 3.0 | 7.7 |
| 6.5 | 16.3 |
| 10.0 | 48.1 |

TABLE 6

Combination activity of MOR00208 and venetoclax

| Actual MOR00208 Dose [µg/mL] | Actual Venetoclax Dose [µM] | Actual MOR00208 + Venetoclax Effect [% dead cells] | Theoretical MOR00208 Dose [µg/mL] | Theoretical Venetoclax Dose [µM] | Combination Index |
|---|---|---|---|---|---|
| 1.50E−05 | 3.0 | 18.1 | 2.90E−05 | 6.4 | 0.99 |
| 1.50E−04 | | 28.6 | 2.18E−04 | 7.9 | 1.07 |
| 1.50E−03 | | 47.5 | 1.52E−03 | 10.2 | 1.28 |
| 1.50E−02 | | 74.9 | 2.79E−01 | 15.4 | 0.25 |
| 1.50E+00 | | 78.1 | * 1.00E+03 | 16.6 | 0.18 |
| 1.50E−06 | 6.5 | 17.9 | 2.67E−05 | 6.4 | 1.08 |
| 1.50E−05 | | 26.2 | 1.57E−04 | 7.5 | 0.96 |
| 1.50E−04 | | 37.8 | 6.02E−04 | 9.0 | 0.97 |
| 1.50E−03 | | 61.3 | 6.52E−03 | 12.2 | 0.76 |
| 1.50E−02 | | 85.8 | * 1.00E+03 | 22.3 | 0.29 |
| 1.50E+00 | | 88.7 | * 1.00E+03 | 29.4 | 0.22 |
| 1.50E−06 | 10.0 | 33.1 | 3.71E−04 | 8.4 | 1.19 |
| 1.50E−05 | | 42.9 | 9.83E−04 | 9.6 | 1.06 |
| 1.50E−04 | | 57.6 | 4.20E−03 | 11.6 | 0.90 |
| 1.50E−03 | | 81.6 | * 1.00E+03 | 18.4 | 0.54 |
| 1.50E−02 | | 95.9 | * 1.00E+03 | 31.0 | 0.32 |
| 1.50E+00 | | 96.0 | * 1.00E+03 | 31.0 | 0.32 |

* Infinite theoretical MOR00208 dose as actual MOR00208 effect saturates below MOR00208 + Venetoclax effect Calculation of Synergism Combination Index (CI) calculations are completed in order to determine synergy of the combination of the exemplified anti-CD19 antibody and venetoclax as compared to MOR00208 and venetoclax alone. Such calculations are described in Ting-Chao Chou, Theoretical Basis, Experimental Design, and Computerized Simulation of Synergism and Antagonism in Drug Combination Studies, Pharmacol Rev 58:621-681 (2006), which is incorporated by reference in its entirety and Chou TC, Talalay P, Quantitative analysis of dose-effect relationships: the combined effects of multiple drugs or enzyme inhibitors. Adv Enzyme Regul 22: 27-55 (1984), which is incorporated by reference in its entirety. The methods of Chou-Talalay are carried out using the CI-isobol method.

Median Effect Equation

The median-effect equation models the effect of an inhibitor (such as a drug) as $F_a/F_u=(D/D50)^m$, where D is the dose, $F_a$ and $F_u$ is the fraction of the system affected and unaffected by the dose D ($F_a+F_u=1$); D50 is the dose producing the median effect (e.g. IC50, ED50, LD50). The constant m determines the shape of the dose-effect curve. We used GraphPad Prism to carry out a nonlinear regression calculation to estimate the parameters m and D50.

CI-Isobol Method

The CI-isobol method provides a quantitative assessment of synergism between drugs. A combination index (CI) is estimated from dose-effect data of single and combined drug treatments. A value of CI less than 1 indicates synergism; CI=1 indicates additive effect; and CI>1 indicates antagonism. Drug interaction (synergism or antagonism) is more pronounced the farther a CI value is from 1. Formally, the combination index (CI) of a combined drug treatment is defined as $CI=D_1/D_{x1}+D_2/D_{x2}$. Here D1 and D2 are the doses of drug 1 and drug 2 of the combination, respectively; and Dx1, and Dx2 is the dose of a treatment with only drug 1 and drug 2 that would give the same effect as that of the combination. The doses Dx1 and Dx2 need to be estimated from the dose-effect data of single drug treatments. Essentially, a median effect equation is fitted to the data of each drug. From the median effect equation of a drug, we can estimate the dose (i.e. D) necessary to produce an effect (i.e. Fa, Fu). The further a point lies from the additive line, the bigger the different between 1 and its CI, thus the stronger the (synergistic or antagonistic) effect is.

Results

Mean (+/−SEM) combination index curves of all three experiments for each venetoclax concentration are shown in FIGS. 6-8. The combination index values indicate clear synergism of the combination of MOR00208 and venetoclax in the specific killing of MEC-1 cells as compared to MOR00208 and venetoclax alone. Very low doses of MOR00208 have little or no effect in the exemplified ADCC cell killing assays. Accoridngly, the CI values at very low doses of MOR00208 show a value at or slightly above 1, which value represents only the acivity of venetoclax. At MOR00208 concentrations, where MOR00208 alone shows normal cell killing activity, clear synergism is shown by the CI values less than 1, which represents the activity of MOR00208 and venetoclax. The highest concentration of MOR00208 exemplified herein is obtained in the ongoing clinical trials, where MOR00208 is dosed at 12 mg/kg once weekly. Accordingly it is believed that the exemplified in vitro model is predictive of activity in humans. Therefore, the combination of MOR00208 and venetoclax should also behave synergistically in the treatment of non-Hodgkin's lymphoma (NHL), chronic lymphoid leukemia (CLL), and acute lymphoblastic leukemia (ALL) in humans.

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein, and thus are considered part of the invention.

Example 2: Efficacy of MOR00208 in Combination with ABT-199 in a Subcutaneous Human Lymphoma Cell Xenograft Model in SCID Mice The efficacy benefit of MOR00208 in combination with venetoclax (ABT-199) was further studied in a SCID mouse model with subcutaneous TOLEDO human lymphoma cell tumors. Tumor growth and mortality were assessed.

Materials & Methods

Toledo cell line and culture medium were purchased and provided by Oncodesign. Tumor cells were grown as monolayer at 37'C in a humidified atmosphe re (5% CO2, 95% air). The culture medium was RPMI 1640 containing 2 mM L-glutamine (ref: BE12-702F, Lonza, Verviers, Belgium) supplemented with 10% fetal bovine serum (ref: P30-1506, Lonza), HBSS (ref: BE10-543F), Glucose (ref: G8769, Sigma, France), Hepes (ref: BE17-737E, Lonza) and Sodium pyruvate (ref: BE13-115E, Lonza). The cells are adherent to plastic flasks. For experimental use, tumor cells were detached from the culture flask by a 5-minute treatment with trypsin-versene (ref: 6E02-007E, Lonza), in Hanks' medium without calcium or magnesium (ref: BE10-543F, Lonza) and neutralized by addition of complete culture medium. The cells were counted in a hemocytometer and their viability was assessed by 0.25% trypan blue exclusion assay.

Tumors were induced by subcutaneous injection of $10 \times 10^6$ of Toledo cells in 200 µl of RPMI 1640 containing matrigel (50:50, v:v, ref: 356237, BD Biosciences, France) into the right flank of SCID mice. At D23, when tumors reached a mean volume of $256 \pm 68$ mm$^3$, 60 mice were randomized according to their individual tumor volume into 6 groups each of 10 animals using Vivo Manager® software (Biosystemes, Couternon, France). A statistical test (analysis of variance, ANOVA) was performed to test for homogeneity between groups. MOR208 was injected intraperitoneally (IP) into the peritoneal cavity of mice. Combined substance was administered by oral gavage (per os, PO) via a gavage tube.

The treatment schedule initiated at D23 was as follows:

Animals from group 1 received one daily PO administration of PEP and one IP injection twice a week of PBS.

Animals from group 2 received daily PO administration of ABT-199 at 20 mg/kg/adm Animals from group 3 received daily PO administration of ABT-199 at 40 mg/kg/adm.

Animals from group 4 received one IP injection of MOR208 at 11 mg/kg/inj on D23, D27, D30, D34, D37 and D41 followed by a single IP injection of MOR208 at 11 mg/kg/inj on D48 (twice a week).

Animals from group 5 received daily PO administration of ABT-199 at 20 mg/kg/adm in combination with IP injections of MOR208 at 11 mg/kg/inj on D23, D27, D30, D34, D37 and D41 and on D48, D51, D55 and D58.

Animals from group 6 received daily PO administration of ABT-199 at 40 mg/kg/adm in combination with two cycles of one IP injection of MOR208 at 11 mg/kg/inj on D23, D27, D30, D34, D37 and D41 and on D48, D51, D55 and D58.

All study data, including animal bodyweight measurements, clinical and mortality records, and treatment were scheduled and recorded on Vivo Manager® database (Biosystemes, Dijon, France). The viability and behavior were recorded every day. Body weights and tumor volume were measured twice a week. The length and width of the tumor were measured twice a week with calipers and the volume of the tumor was estimated by the formula:

$$\text{Tumor volume} = \frac{\text{width}^2 \times \text{length}}{2}$$

Results

Figure 9:
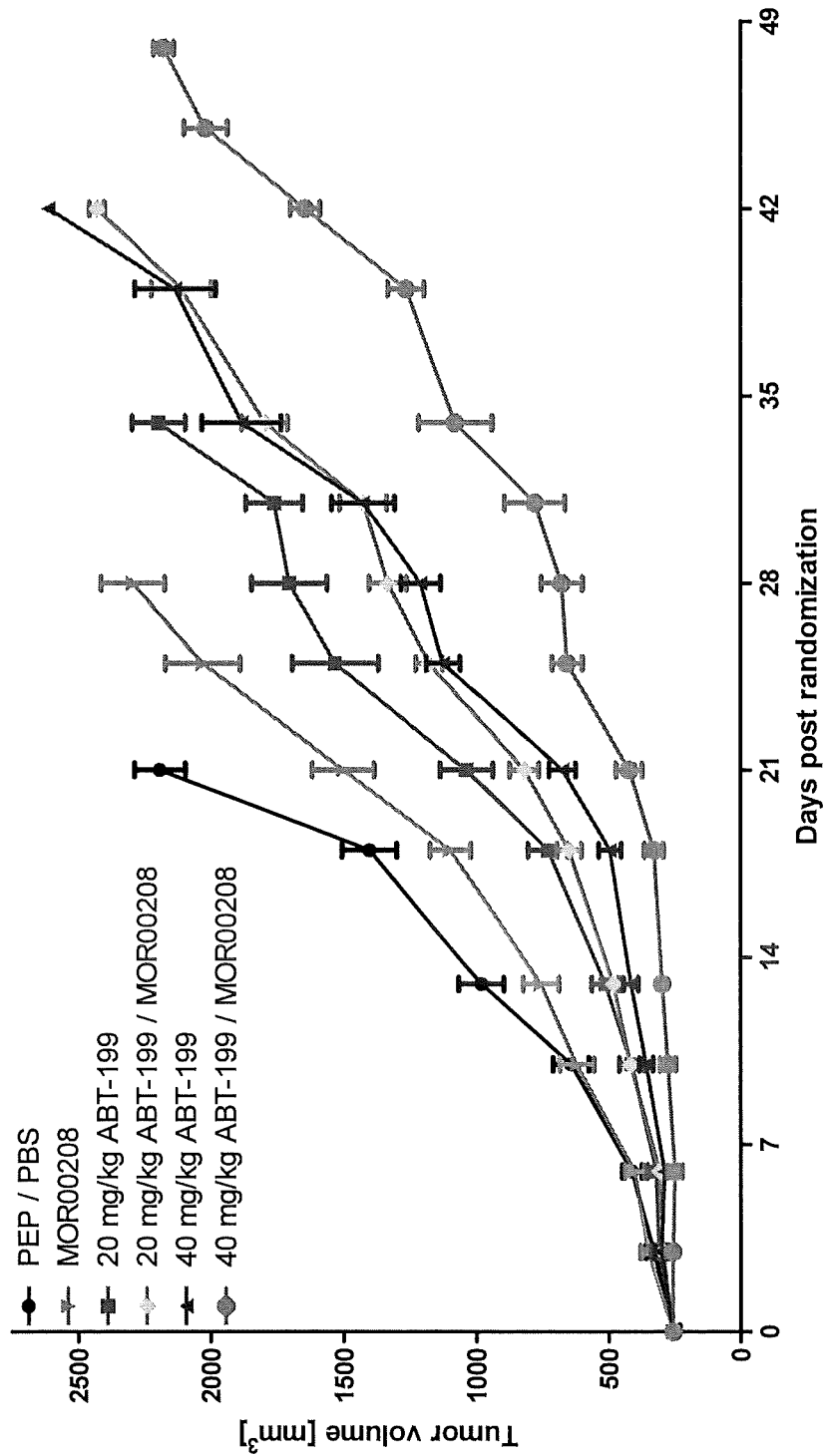
FIG. 9 MOR00208 in combination with ABT-199 showed superior reduction of tumor growth compared to either mono therapy in a s.c. Toledo SCID mouse model. Group mean values±standard error of mean (SEM) are depicted. Asterics indicated statistical siginificance of the tumor doubling time of the combination treatment vs the MOR0028 single treatment or the respective ABT-199 single treatment: * p-value<0.05,  p-value<0.01 and ** p-value<0.0001. Treatment started upon randomization at a median tumor volume of 266 mm³ (123-406 mm³) 23 days after tumor injection. MOR00208 (11 mg/kg) was administered by intraperitoneal injection (i.p.) twice weekly. ABT-199 (20 or 40 mg/kg) was administered by per os (p.o.) daily.
Figure 10:
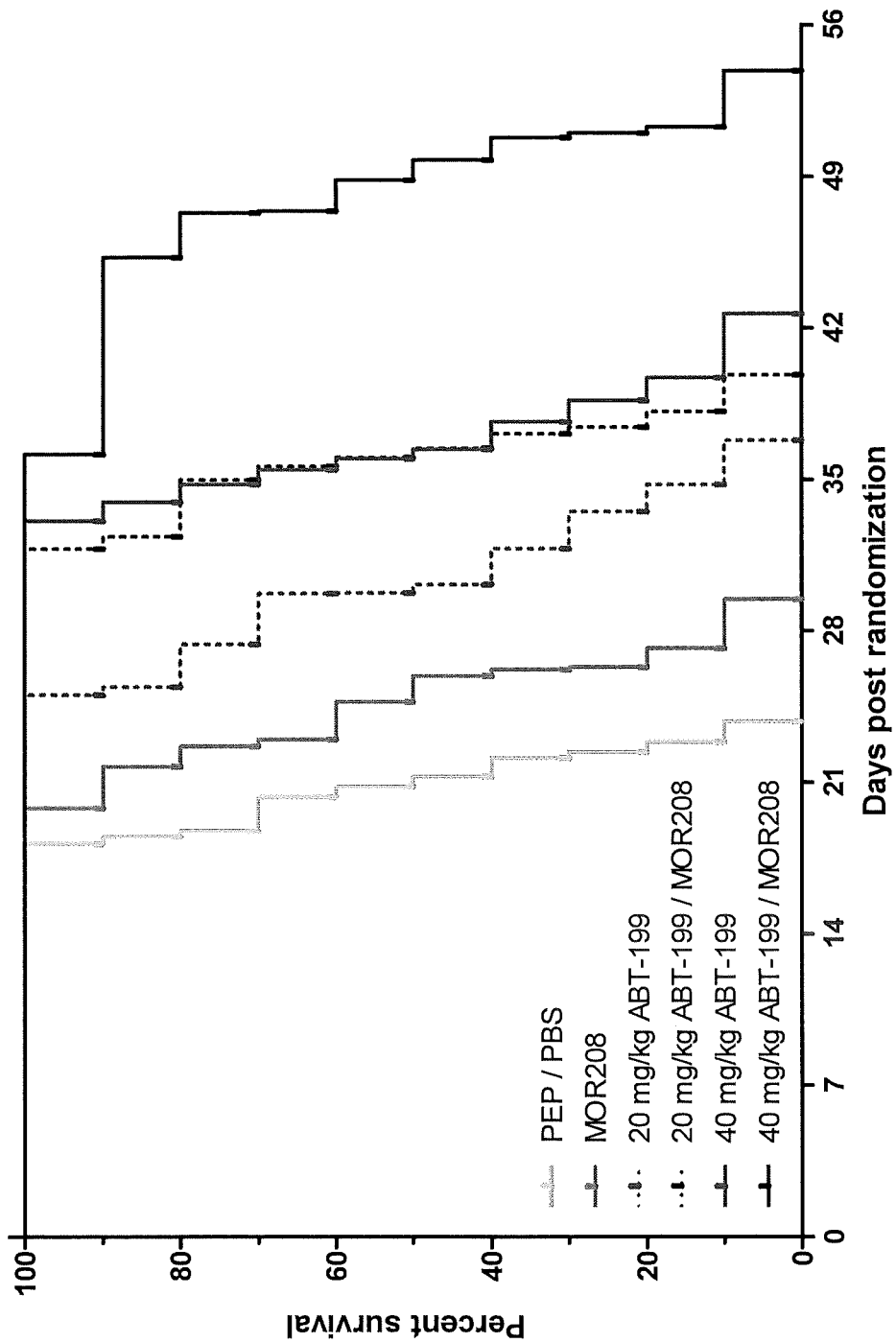
FIG. 10 MOR00208 in combination with ABT showed superior median survival compared to either monotherapy in a s.c. Toledo SCID mouse model. The Kaplan-Meier curves depict the survival from randomization until the humane endpoint (Tumor volume of 2000 mm³). Treatment started upon randomization at a median tumor volume of 266 mm³ (123-406 mm³) 23 days after tumor injection. MOR00208 (11 mg/kg) was administered by intraperitoneal injection (i.p.) twice weekly. ABT-199 (20 or 40 mg/kg) was administered by per os (p.o.) daily.

The combination treatment of MOR00208 and ABT-199 at a dose of 20 and 40 mg/kg resulted in a superior and statistically significant inhibition of the growth of the Toledo lymphoma cells compared to the vehicle control and both monotherapy regimens. The anti-tumor effect of MOR00208 in combination with ABT-199 shows even more pronounced when the survival of the mice from randomization until the humane endpoint (tumor volume of 2000 mm3) is analyzed. The median survival and the respective increased life span of the combination groups were superior compared to the respective monotherapies. A further characterisation of the combination effect categorizes the result of the combination of MOR00208 as potentiation since the effect of the combination is bigger than the sum of the repesctive monotherapies (FIG. 9, Table 7, FIG. 10, Table 8).

TABLE 7

Effect of MOR00208 and ABT-199 alone and in combination on median survival in a s.c. Toledo SCID mouse model.

| Group | Treatment | Median Tumor Doubling Time (Days) | Median % Increase in Doubling Time (IDT)[§] | Evaluation of combinatorial effects |
|---|---|---|---|---|
| 1 | PEP/PBS | 6.8 | n.a. | n.a. |
| 4 | MOR00208 11 mg/kg | 8.0 | 18 | n.a. |
| 2 | ABT-199 20 mg/kg | 9.6[a] | 44 | n.a. |
| 3 | ABT-199 40 mg/kg | 11.1[a] | 64 | n.a. |
| 5 | ABT-199 20 mg/kg & MOR00208 11 mg/kg | 11.5[b] | 70 | Synergy[c] |
| 6 | ABT-199 40 mg/kg & MOR00208 11 mg/kg | 13.5[b] | 100 | Synergy[d] |

[§]vs. PEP/PBS Control,
[a]significantly different to PBS Control,
[b] significantly different to vehicle control and respective monotherapy groups,
[c]Synergy vs. the respective monotherapy groups as IDT Combination ABT-199 20 mg/kg & MOR00208 11 mg/kg (70%) > sum of the effects of the respective monotherapy groups IDT ABT-199 20 mg/kg (44%) + IDT MOR00208 11 mg/kg (18%) = 62%.
[d]Synergy vs. the respective monotherapy groups as IDT Combination ABT-199 40 mg/kg & MOR00208 11 mg/kg (100%) > sum of the effects of the respective monotherapy groups IDT ABT-199 40 mg/kg (64%) + IDT MOR00208 11 mg/kg (18%) = 82%. (

TABLE 8

Effect of MOR00208 and ABT-199 alone and in combination on median survival in a s.c. Toledo SCID mouse model.

| Group | Treatment | Median Survival (Days Post-Randomization) | Median % Increase in Lifespan (ILS)§ | Evaluation of combinatorial effects |
|---|---|---|---|---|
| 1 | PEP/PBS | 21.0 | n.a. | n.a. |
| 4 | MOR00208 11 mg/kg | 25.3 | 20 | n.a. |
| 2 | ABT-199 20 mg/kg | 30.0[a] | 43 | n.a. |
| 3 | ABT-199 40 mg/kg | 36.2[a] | 72 | n.a. |
| 5 | ABT-199 20 mg/kg & MOR00208 11 mg/kg | 36.2[b] | 79 | Synergy[c] |
| 6 | ABT-199 40 mg/kg & MOR00208 11 mg/kg | 49.3[b] | 134 | Synergy[d] |

§vs. PEP/PBS Control,
[a] significantly different to PBS Control,
[b] significantly different to vehicle control and respective monotherapy groups,
[c] Synergy vs. the respective monotherapy groups as ILS Combination ABT-199 20 mg/kg & MOR00208 11 mg/kg (72%) > sum of the effects of the respective monotherapy groups ILS ABT-199 20 mg/kg (43%) + ILS MOR00208 11 mg/kg (20%) = 63%.
[d] Synergy vs. the respective monotherapy groups as ILS Combination ABT-199 40 mg/kg & MOR00208 11 mg/kg (134%) > sum of the effects of the respective monotherapy groups ILS ABT-199 40 mg/kg (72%) + ILS MOR00208 11 mg/kg (20%) = 92%.

We claim:

1. A method for treatment of chronic lymphocytic leukemia, acute lymphoblastic leukemia or non-Hodgkin's lymphoma, said method comprising administering to a human subject with chronic lymphocytic leukemia, acute lymphoblastic leukemia or non-Hodgkin's lymphoma a therapeutically effective amount of a combination comprising an antibody specific for CD19 wherein said antibody comprises an HCDR1 region comprising sequence SYVMH (SEQ ID NO: 1), an HCDR2 region comprising sequence NPYNDG (SEQ ID NO: 2), an HCDR3 region comprising sequence GTYYYGTRVFDY (SEQ ID NO: 3), an LCDR1 region comprising sequence RSSKSLQNVNGNTYLY (SEQ ID NO: 4), an LCDR2 region comprising sequence RMSNLNS (SEQ ID NO: 5), and an LCDR3 region comprising sequence MQHLEYPIT (SEQ ID NO: 6) and venetoclax.

2. The method of claim 1, wherein the non-Hodgkin's lymphoma is selected from the group consisting of follicular lymphoma, small lymphocytic lymphoma, mucosa-associated lymphoid tissue lymphoma, marginal zone lymphoma, diffuse large B cell lymphoma, Burkitt's lymphoma, and mantle cell lymphoma.

3. The method according to claim 1, wherein the antibody has ADCC activity.

4. The method according to claim 1, wherein the antibody comprises a variable heavy chain comprising the sequence EVQLVESGGGLVKPGGSLKLSCAASGYTFTSYVMHWVRQAPGKGLEWIGYINPYNDGTKYNEKFQGRVTISSDKSISTAYMELSSLRSEDTAMYYCARGTYYYGTRVFDYWG QGTLVTVSS (SEQ ID NO: 10) and a variable light chain comprising the sequence DIVMTQSPATLSLSPGERATLSCRSSKSLQNVNGNTYLYWFQQKPGQSPQLLIYRMSNLNSGVPDRFSGSGSGTEFTLTISSLEPEDFAVYYCMQHLEYPITFGAGTKLEIK (SEQ ID NO: 11).

5. The method according to claim 1, wherein the antibody comprises a heavy chain constant domain comprising the sequence ASTKGPSVFPLAPSSKSTSGGTAALGCLVKDYFPEPVTVSWNSGALTSGVHTFPAVLQSSGLY SLSS- WTVPSSSLGTQTYICNVNHKPSNTKVDKKVEPKSCDKTHTCPPCPAPELLGGPDVFLFP PKPKDTLMISRTPEVTCVVVDVSHEDPEVQFNWYVDGVEVHNAKTKPREEQFNSTFRVVSVLT WHQDWLNGKEYKCKVSNKALPAPEEKTISKTKGQPREPQVYTLPPSREEMTKNQVSLTCLVK GFYPSDIAVEWESNGQPENNYKTTPPMLDSDGSFFLYSKLTVDKSRWQQGNVFSCSVMHEALHNHYTQKSLSLSPGK (SEQ ID NO: 12).

6. The method according to claim 1, wherein the antibody comprises a light chain constant domain comprising the sequence RTVAAPSVFI FPPSDEQLKSGTASWCLLN- NFYPREAKVQWKVDNALQSGNSQESVTEQDSKD STYSLSSTLTLSKADYEKHKVYACEVTHQGLSSPVTKSFNRGEC (SEQ ID NO: 13).

7. The method according to claim 1, wherein said antibody specific for CD19 and venetoclax are administered separately.

8. The method according to claim 1, wherein venetoclax is administered prior to administration of the antibody specific for CD19.

9. The method according to claim 1, wherein said antibody specific for CD19 and venetoclax are administered simultaneously.

10. The method according to claim 1, wherein said antibody specific for CD19 and venetoclax are administered at a time where both drugs are active in the subject at the same time.

11. The method according to claim 1 wherein said antibody is administered at 11 mg/kg/injection or more.

12. The method according to claim 1, wherein the human subject has chronic lymphocytic leukemia.

13. The method according to claim 1, wherein the human subject has acute lymphoblastic leukemia.

14. The method according to claim 1, wherein the human subject has non- Hodgkin's lymphoma.

15. The method according to claim 12, wherein the antibody comprises a variable heavy chain comprising the sequence EVOLVESGGGLVKPGGSLKLSCAASGYTFTSYVMHWVRQAPGKGLEWIGYINPYNDGT KYNEKFQGRVTISSDKSISTAYMELSSLRSEDTAMYYCARGTYYYGTRVFDYWGQGTL VTVSS (SEQ ID NO:10) and a variable light chain comprising the sequence DIVMTQSPATLSLSPGERATLSCRSSKSLQNVNGNTYLYWFQQKPGQSPQLLIYRMSNL NSGVPDRFSGSGSGTEFTLTISSLEPEDFAVYYCMQHLEYPITFGAGTKLEIK (SEQ ID NO: 11).

16. The method according to claim 15, wherein the antibody comprises a heavy chain constant domain comprising the sequence ASTKGPSVFPLAPSSKSTSGGTAALGCLVKDYFPEPVTVSWNSGALTSGVHTFPAVLQSS GLYSLSSVVTVPSSSLGTQTYICNVNHKPSNTKVDKKVEPKSCDKTHTCPPCPAPELLGGPDVFLFPPKPKDTLMISRTPEVTCVVVDVSHEDPEVQFNWYVDGVEVHNAKTKPREEQFNSTFRVVSVLTVVHQDWL NGKEYKCKVSNKALPAPEEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK (SEQ ID NO: 12) and a light chain constant domain comprising the sequence RTVAAPSVFIFPPSDEQLKSGTASVVCLLNNFYPREAKVQWKVDNALQSGNSQESVTEQ DSKDSTYSLSSTLTLSKADYEKHKVYACEVTHQGLSSPVTKSFNRGEC (SEQ ID NO:13).

17. The method according to claim 13, wherein the antibody comprises a variable heavy chain comprising the sequence EVOLVESGGGLVKPGGSLKLSCAASGYTFTSYVMHWVRQAPGKGLEWIGYINPYNDGT KYNEKFQGRVTISSDKSISTAYMELSSLRSEDTAMYYCARGTYYYGTRVFDYWGQGTL VTVSS (SEQ ID NO:10) and a variable light chain comprising the sequence DIVMTQSPATLSLSPGERATLSCRSSKSLQNVNGNTYLYWFQQKPGQSPQLLIYRMSNL NSGVPDRFSGSGSGTEFTLTISSLEPEDFAVYYCMQHLEYPITFGAGTKLEIK (SEQ ID NO: 11).

18. The method according to claim 17, wherein the antibody comprises a heavy chain constant domain comprising the sequence ASTKGPSVFPLAPSSKSTSGGTAALGCLVKDYFPEPVTVSWNSGALTSGVHTFPAVLQSS GLYSLSSVVTVPSSSLGTQTYICNVNHKPSNTKVDKKVEPKSCDKTHTCPPCPAPELLGGPDVFLFPPKPKDTLMISRTPEVTCVVVDVSHEDPEVQFNWYVDGVEVHNAKTKPREEQF NSTFRVVSVLTVVHQDWLNGKEYKCKVSNKALPAPEEKTISKTKGQPREPQVYTLPPSR EEMTKNQVSLTCLVKGFYPSDIAVEWESNGQPENNYKTTPPMLDSDGSFFLYSKLTVDK SRWQQGNVFSCSVMHEALHNHYTQKSLSLSPGK (SEQ ID NO:12) and a light chain constant domain comprising the sequence RTVAAPSVFIFPPSDEQLKSGTASVVCLLNNFYPREAKVQWKVDNALQSGNSQESVTEQ DSKDSTYSLSSTLTLSKADYEKHKVYACEVTHQGLSSPVTKSFNRGEC (SEQ ID NO:13).

19. The method according to claim 14, wherein the antibody comprises a variable heavy chain comprising the sequence EVQLVESGGGLVKPGGSLKLSCAASGYTFTSYVMHWVRQAPGKGLEWIGYINPYNDGT KYNEKFQGRVTISSDKSISTAYMELSSLRSEDTAMYYCARGTYYYGTRVFDYWGQGTL VTVSS (SEQ ID NO:10) and a variable light chain comprising the sequence DIVMTQSPATLSLSPGERATLSCRSSKSLQNVNGNTYLYWFQQKPGQSPQLLIYRMSNLNSGVPDRFSGSGSGT- EFTLTISSLEPEDFAVYYCMQHLEYPITFGAGTKLEIK (SEQ ID NO: 11).

20. The method according to claim 19, wherein the antibody comprises a heavy chain constant domain comprising the sequence ASTKGPSVFPLAPSSKSTSGGTAALGCLVKDYFPEPVTVSWNSGALTSGVHTFPAVLQSS GLYSLSSVVTVPSSSLGTQTYICNVNHKPSNTKVDKKVEPKSCDKTHTCPPCPAPELLGGPDVFLFPPKPKDTLMISRTPEVTCVVVDVSHEDPEVQFNWYVDGVEVHNAKTKPREEQFNSTFRVVSVLTVVHQDWLNGKEYKCKVSNKALPAPEEKTISKTKGQPREPQVYTLPPSR EEMTKNQVSLTCLVKGFYPSDIAVEWESNGQPENNYKTTPPMLDSDGSFFLYSKLTVDK SRWQQGNVFSCSVMHEALHNHYTQKSLSLSPGK (SEQ ID NO:12) and a light chain constant domain comprising the sequence RTVAAPSVFIFPPSDEQLKSGTASVVCLLNNFYPREAKVQWKVDNALQSGNSQESVTEQ DSKDSTYSLSSTLTLSKADYEKHKVYACEVTHQGLSSPVTKSFNRGEC (SEQ ID NO:13).

* * * * *

UNITED STATES PATENT AND TRADEMARK OFFICE
CERTIFICATE OF CORRECTION

PATENT NO. : 12,358,983 B2
APPLICATION NO. : 16/342645
DATED : July 15, 2025
INVENTOR(S) : Jan Endell et al.

Page 1 of 1

It is certified that error appears in the above-identified patent and that said Letters Patent is hereby corrected as shown below:

In the Claims

Column 41, Line 1, Claim 5, delete "WTVP" and insert -- VVTVP --;

Column 41, Line 4, Claim 5, delete "T WH" and insert -- TVVH --;

Column 41, Line 11, Claim 6, delete "ASWC" and insert -- ASVVC --;

Column 41, Line 35, Claim 14, delete "non- Hodgkin's" and insert -- non-Hodgkin's --;

Column 41, Line 38, Claim 15, delete "EVOL" and insert -- EVQL --;

Column 42, Line 6, Claim 17, delete "EVOL" and insert -- EVQL --.

Signed and Sealed this
Second Day of September, 2025

Coke Morgan Stewart
*Acting Director of the United States Patent and Trademark Office*

SEQUENCE LISTING

```
<160> NUMBER OF SEQ ID NOS: 15

<210> SEQ ID NO 1
<211> LENGTH: 5
<212> TYPE: PRT
<213> ORGANISM: Artificial sequence
<220> FEATURE:
<223> OTHER INFORMATION: synthetic construct

<400> SEQUENCE: 1

Ser Tyr Val Met His
1               5

<210> SEQ ID NO 2
<211> LENGTH: 6
<212> TYPE: PRT
<213> ORGANISM: Artificial sequence
<220> FEATURE:
<223> OTHER INFORMATION: synthetic construct

<400> SEQUENCE: 2

Asn Pro Tyr Asn Asp Gly
1               5

<210> SEQ ID NO 3
<211> LENGTH: 12
<212> TYPE: PRT
<213> ORGANISM: Artificial sequence
<220> FEATURE:
<223> OTHER INFORMATION: synthetic construct

<400> SEQUENCE: 3

Gly Thr Tyr Tyr Tyr Gly Thr Arg Val Phe Asp Tyr
1               5                   10

<210> SEQ ID NO 4
<211> LENGTH: 16
<212> TYPE: PRT
<213> ORGANISM: Artificial sequence
<220> FEATURE:
<223> OTHER INFORMATION: synthetic construct

<400> SEQUENCE: 4

Arg Ser Ser Lys Ser Leu Gln Asn Val Asn Gly Asn Thr Tyr Leu Tyr
1               5                   10                  15
```

<210> SEQ ID NO 5
<211> LENGTH: 7
<212> TYPE: PRT
<213> ORGANISM: Artificial sequence
<220> FEATURE:
<223> OTHER INFORMATION: synthetic construct

<400> SEQUENCE: 5

Arg Met Ser Asn Leu Asn Ser
1               5

<210> SEQ ID NO 6
<211> LENGTH: 9
<212> TYPE: PRT
<213> ORGANISM: Artificial sequence
<220> FEATURE:
<223> OTHER INFORMATION: synthetic construct

<400> SEQUENCE: 6

Met Gln His Leu Glu Tyr Pro Ile Thr
1               5

<210> SEQ ID NO 7
<211> LENGTH: 556
<212> TYPE: PRT
<213> ORGANISM: Homo sapiens
<220> FEATURE:
<223> OTHER INFORMATION: CD19

<400> SEQUENCE: 7

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
            245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
            275                 280                 285

Gly Trp Lys Val Ser Ala Val Thr Leu Ala Tyr Leu Ile Phe Cys Leu
            290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
            325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
            355                 360                 365

Ala Gly Leu Gly Gly Thr Ala Pro Ser Tyr Gly Asn Pro Ser Ser Asp
            370                 375                 380

Val Gln Ala Asp Gly Ala Leu Gly Ser Arg Ser Pro Pro Gly Val Gly
385                 390                 395                 400

Pro Glu Glu Glu Glu Gly Glu Gly Tyr Glu Glu Pro Asp Ser Glu Glu
            405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
            435                 440                 445

Pro Glu Asp Glu Asp Ser Phe Ser Asn Ala Glu Ser Tyr Glu Asn Glu
450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
            485                 490                 495

Ser Gln Ser Tyr Glu Asp Met Arg Gly Ile Leu Tyr Ala Ala Pro Gln
            500                 505                 510

Leu Arg Ser Ile Arg Gly Gln Pro Gly Pro Asn His Glu Glu Asp Ala
            515                 520                 525

Asp Ser Tyr Glu Asn Met Asp Asn Pro Asp Gly Pro Asp Pro Ala Trp
            530                 535                 540

Gly Gly Gly Gly Arg Met Gly Thr Trp Ser Thr Arg
545                 550                 555

<210> SEQ ID NO 8
<211> LENGTH: 450
<212> TYPE: PRT
<213> ORGANISM: Artificial sequence
<220> FEATURE:
<223> OTHER INFORMATION: Heavy chain RefMab33

<400> SEQUENCE: 8

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
            35                  40                  45

```
Trp Leu Ala Asp Ile Trp Trp Asp Asp Lys His Tyr Asn Pro Ser
 50                  55                  60

Leu Lys Asp Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                 85                  90                  95

Cys Ala Arg Asp Met Ile Phe Asn Phe Tyr Phe Asp Val Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Asp Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Phe Arg
290                 295                 300

Val Val Ser Val Leu Thr Val Val His Gln Asp Trp Leu Asn Gly Lys
305                 310                 315                 320

Glu Tyr Lys Cys Lys Val Ser Asn Lys Ala Leu Pro Ala Pro Glu Glu
                325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
450
```

<210> SEQ ID NO 9
<211> LENGTH: 213
<212> TYPE: PRT
<213> ORGANISM: Artificial sequence
<220> FEATURE:
<223> OTHER INFORMATION: Light chain RefMab33

<400> SEQUENCE: 9

```
Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 10
<211> LENGTH: 121
<212> TYPE: PRT
<213> ORGANISM: Artificial sequence
<220> FEATURE:
<223> OTHER INFORMATION: synthetic construct

<400> SEQUENCE: 10

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95
```

```
Ala Arg Gly Thr Tyr Tyr Gly Thr Arg Val Phe Asp Tyr Trp Gly
                100                 105                 110

Gln Gly Thr Leu Val Thr Val Ser Ser
        115                 120
```

<210> SEQ ID NO 11
<211> LENGTH: 112
<212> TYPE: PRT
<213> ORGANISM: Artificial sequence
<220> FEATURE:
<223> OTHER INFORMATION: synthetic construct

<400> SEQUENCE: 11

```
Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Val
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
            100                 105                 110
```

<210> SEQ ID NO 12
<211> LENGTH: 330
<212> TYPE: PRT
<213> ORGANISM: Artificial sequence
<220> FEATURE:
<223> OTHER INFORMATION: synthetic construct

<400> SEQUENCE: 12

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Gln Phe Asn Trp
145                 150                 155                 160

Tyr Val Asp Gly Val Glu Val His Asn Ala Lys Thr Lys Pro Arg Glu
```

```
                165                 170                 175
Glu Gln Phe Asn Ser Thr Phe Arg Val Val Ser Val Leu Thr Val Val
            180                 185                 190
His Gln Asp Trp Leu Asn Gly Lys Glu Tyr Lys Cys Lys Val Ser Asn
            195                 200                 205
Lys Ala Leu Pro Ala Pro Glu Lys Thr Ile Ser Lys Thr Lys Gly
            210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
            245                 250                 255
Pro Ser Asp Ile Ala Val Glu Trp Glu Ser Asn Gly Gln Pro Glu Asn
            260                 265                 270
Asn Tyr Lys Thr Thr Pro Pro Met Leu Asp Ser Asp Gly Ser Phe Phe
            275                 280                 285
Leu Tyr Ser Lys Leu Thr Val Asp Lys Ser Arg Trp Gln Gln Gly Asn
            290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
            325                 330

<210> SEQ ID NO 13
<211> LENGTH: 107
<212> TYPE: PRT
<213> ORGANISM: Artificial sequence
<220> FEATURE:
<223> OTHER INFORMATION: synthetic construct

<400> SEQUENCE: 13

Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105

<210> SEQ ID NO 14
<211> LENGTH: 451
<212> TYPE: PRT
<213> ORGANISM: Artificial sequence
<220> FEATURE:
<223> OTHER INFORMATION: synthetic construct

<400> SEQUENCE: 14

Glu Val Gln Leu Val Glu Ser Gly Gly Gly Leu Val Lys Pro Gly Gly
1               5                   10                  15
Ser Leu Lys Leu Ser Cys Ala Ala Ser Gly Tyr Thr Phe Thr Ser Tyr
            20                  25                  30
```

-continued

```
Val Met His Trp Val Arg Gln Ala Pro Gly Lys Gly Leu Glu Trp Ile
         35                  40                  45

Gly Tyr Ile Asn Pro Tyr Asn Asp Gly Thr Lys Tyr Asn Glu Lys Phe
 50                  55                  60

Gln Gly Arg Val Thr Ile Ser Ser Asp Lys Ser Ile Ser Thr Ala Tyr
 65                  70                  75                  80

Met Glu Leu Ser Ser Leu Arg Ser Glu Asp Thr Ala Met Tyr Tyr Cys
                 85                  90                  95

Ala Arg Gly Thr Tyr Tyr Gly Thr Arg Val Phe Asp Tyr Trp Gly
             100                 105                 110

Gln Gly Thr Leu Val Thr Val Ser Ser Ala Ser Thr Lys Gly Pro Ser
             115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                 165                 170                 175

Val Leu Gln Ser Ser Gly Leu Tyr Ser Leu Ser Ser Val Val Thr Val
             180                 185                 190

Pro Ser Ser Ser Leu Gly Thr Gln Thr Tyr Ile Cys Asn Val Asn His
             195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Asp Val Phe Leu Phe Pro Pro Lys Pro Lys Asp Thr Leu Met
                 245                 250                 255

Ile Ser Arg Thr Pro Glu Val Thr Cys Val Val Val Asp Val Ser His
             260                 265                 270

Glu Asp Pro Glu Val Gln Phe Asn Trp Tyr Val Asp Gly Val Glu Val
             275                 280                 285

His Asn Ala Lys Thr Lys Pro Arg Glu Glu Gln Phe Asn Ser Thr Phe
290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Ala Leu Pro Ala Pro Glu
                 325                 330                 335

Glu Lys Thr Ile Ser Lys Thr Lys Gly Gln Pro Arg Glu Pro Gln Val
             340                 345                 350

Tyr Thr Leu Pro Pro Ser Arg Glu Glu Met Thr Lys Asn Gln Val Ser
             355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                 405                 410                 415

Asp Lys Ser Arg Trp Gln Gln Gly Asn Val Phe Ser Cys Ser Val Met
             420                 425                 430

His Glu Ala Leu His Asn His Tyr Thr Gln Lys Ser Leu Ser Leu Ser
             435                 440                 445

Pro Gly Lys
```

```
<210> SEQ ID NO 15
<211> LENGTH: 219
<212> TYPE: PRT
<213> ORGANISM: Artificial sequence
<220> FEATURE:
<223> OTHER INFORMATION: synthetic construct

<400> SEQUENCE: 15

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Val
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```